United States Patent
Ni Ghriallais et al.

(10) Patent No.: US 11,484,398 B2
(45) Date of Patent: Nov. 1, 2022

(54) IMPLANT DELIVERY METHODS

(71) Applicant: ProVerum Limited, Dublin (IE)

(72) Inventors: Riona Ni Ghriallais, Dublin (IE); Conor Harkin, Dublin (IE)

(73) Assignee: ProVerum Limited, Dublin (IE)

( * ) Notice: Subject to any disclaimer, the term of this patent is extended or adjusted under 35 U.S.C. 154(b) by 0 days.

(21) Appl. No.: 17/654,642

(22) Filed: Mar. 14, 2022

(65) Prior Publication Data

US 2022/0192813 A1   Jun. 23, 2022

Related U.S. Application Data

(63) Continuation of application No. 16/692,347, filed on Nov. 22, 2019, now Pat. No. 11,273,025.

(51) Int. Cl.
*A61F 2/04*   (2013.01)
*A61F 2/966*   (2013.01)
*A61B 1/307*   (2006.01)

(52) U.S. Cl.
CPC .............. *A61F 2/04* (2013.01); *A61F 2/966* (2013.01); *A61B 1/307* (2013.01); *A61F 2002/047* (2013.01)

(58) Field of Classification Search
CPC .... A61F 2/04; A61F 2/95; A61F 2/966; A61F 2002/047; A61F 2/962
USPC ................... 623/1.11–1.15, 23.64
See application file for complete search history.

(56) References Cited

U.S. PATENT DOCUMENTS

| | | | |
|---|---|---|---|
| 4,580,568 A | 4/1986 | Gianturco | |
| 4,830,003 A | 5/1989 | Wolff et al. | |
| 5,035,706 A | 7/1991 | Gianturco et al. | |
| 5,159,920 A | 11/1992 | Condon et al. | |
| 5,269,802 A | 12/1993 | Garber | |
| 5,292,331 A | 3/1994 | Boneau | |
| 5,591,277 A | 1/1997 | Braunheim | |
| 5,599,325 A * | 2/1997 | Ju ..................... | A61M 25/0045 604/524 |
| 5,674,278 A * | 10/1997 | Boneau ..................... | A61F 2/86 606/195 |
| 5,697,967 A | 12/1997 | Dinh et al. | |
| 5,782,838 A | 7/1998 | Beyar et al. | |
| 5,830,179 A | 11/1998 | Mikus et al. | |

(Continued)

FOREIGN PATENT DOCUMENTS

| | | |
|---|---|---|
| BE | 892016 | 5/1982 |
| BE | 1015962 | 12/2005 |

(Continued)

OTHER PUBLICATIONS

International Search Report and Written Opinion issued in PCT Application No. PCT/EP2020/083102, dated Mar. 9, 2021.

*Primary Examiner* — Suzette J Gherbi
(74) *Attorney, Agent, or Firm* — Knobbe Martens Olson & Bear, LLP

(57) ABSTRACT

Aspects of the present invention relate to a method for locating an expandable implant for treating BPH within the prostatic urethra of a patient. The delivery device comprises an inner tube and an outer sleeve moveable relative to the inner tube between a stored position and a deployed position. The outer sleeve surrounds the inner tube to define an annulus therebetween and the expandable implant is retained within the annulus when the outer sleeve is in the stored position.

27 Claims, 26 Drawing Sheets

(56) References Cited

U.S. PATENT DOCUMENTS

| | | | |
|---|---|---|---|
| 6,093,194 | A | 7/2000 | Mikus et al. |
| 6,110,199 | A | 8/2000 | Walak |
| 6,929,663 | B2 | 8/2005 | Rioux et al. |
| 7,112,226 | B2 | 9/2006 | Gellman |
| 8,591,569 | B2 | 11/2013 | Shin et al. |
| 8,603,187 | B2 | 12/2013 | Kilemnik et al. |
| 9,005,183 | B2 | 4/2015 | Harkins, Jr. |
| 9,114,039 | B2 | 8/2015 | Jordan et al. |
| 9,333,102 | B2 | 5/2016 | Yachia et al. |
| 9,848,905 | B2 | 12/2017 | Kilemnik |
| 9,968,479 | B2 | 5/2018 | Harkins, Jr. |
| 10,004,584 | B2 | 6/2018 | Bartning et al. |
| 10,035,005 | B2 | 7/2018 | Bar-On et al. |
| 10,058,718 | B2 | 8/2018 | Sethuraman et al. |
| 10,478,283 | B2 | 11/2019 | Bachar |
| 10,507,122 | B2 | 12/2019 | Bachar |
| 10,682,245 | B2 * | 6/2020 | Harkin ............... A61F 2/848 |
| 10,881,539 | B2 * | 1/2021 | Harkin ............... A61M 29/02 |
| 11,027,106 | B2 | 6/2021 | Bachar |
| 11,241,312 | B2 * | 2/2022 | Simonin ............. A61F 2/2433 |
| 11,273,025 | B2 * | 3/2022 | Ghriallais ........... A61F 2/966 |
| 2002/0156394 | A1 | 10/2002 | Mehrotra et al. |
| 2006/0100688 | A1 | 5/2006 | Jordan et al. |
| 2006/0136031 | A1 * | 6/2006 | Gallo ................. A61F 2/915 623/1.11 |
| 2007/0077266 | A1 | 4/2007 | Egashira |
| 2007/0163668 | A1 * | 7/2007 | Arbefeuille ........ A61F 2/07 74/67 |
| 2009/0171442 | A1 | 7/2009 | Young et al. |
| 2009/0210045 | A1 | 8/2009 | Sorensen et al. |
| 2009/0312667 | A1 | 12/2009 | Utsunomiya et al. |
| 2010/0137893 | A1 | 6/2010 | Kilemnick et al. |
| 2010/0152835 | A1 * | 6/2010 | Orr ..................... A61F 2/06 623/1.15 |
| 2011/0301690 | A1 | 12/2011 | Giasolli |
| 2012/0179086 | A1 | 7/2012 | Shank |
| 2012/0290065 | A1 | 11/2012 | Li et al. |
| 2014/0012192 | A1 | 1/2014 | Bar-On et al. |
| 2014/0188249 | A1 | 7/2014 | Pendleton et al. |
| 2014/0257020 | A1 | 9/2014 | Smith et al. |
| 2015/0257908 | A1 | 9/2015 | Chao et al. |
| 2015/0374408 | A1 | 12/2015 | Ogdahl et al. |
| 2016/0007987 | A1 | 1/2016 | Catanese, III et al. |
| 2016/0262862 | A1 | 9/2016 | Fischer |
| 2016/0317180 | A1 | 11/2016 | Kilemnik |
| 2017/0135830 | A1 | 5/2017 | Harkin et al. |
| 2017/0165062 | A1 * | 6/2017 | Rothstein ........... A61F 2/966 |
| 2018/0028222 | A1 | 2/2018 | Kilemnik |
| 2018/0235651 | A1 | 8/2018 | Kilemnik |
| 2018/0280669 | A1 | 10/2018 | Shlomovitz et al. |
| 2018/0318114 | A1 | 11/2018 | Huang et al. |
| 2018/0325705 | A1 | 11/2018 | Harkin et al. |
| 2018/0344995 | A1 | 12/2018 | Bar-On et al. |
| 2019/0295444 | A1 | 9/2019 | Zunke et al. |
| 2019/0298334 | A1 | 10/2019 | Catanese, III et al. |
| 2020/0022692 | A1 | 1/2020 | Lamson et al. |
| 2020/0315823 | A1 * | 10/2020 | Harkin ............... A61F 2/04 |
| 2021/0022594 | A1 | 1/2021 | Jen et al. |
| 2021/0052854 | A1 * | 2/2021 | Tavallaei ........... A61M 25/09041 |
| 2021/0059704 | A1 | 3/2021 | Kilemnik |
| 2021/0100666 | A1 | 4/2021 | Harkin et al. |
| 2021/0106730 | A1 | 4/2021 | Koroschetz et al. |
| 2021/0145619 | A1 | 5/2021 | Bly et al. |
| 2021/0154000 | A1 * | 5/2021 | Ghriallais ........... A61F 2/04 |
| 2021/0161642 | A1 | 6/2021 | Jen et al. |
| 2021/0259799 | A1 | 8/2021 | Lessard et al. |
| 2021/0290917 | A1 | 9/2021 | Bachar |
| 2022/0054184 | A9 * | 2/2022 | Rajagopalan ...... A61B 18/06 |
| 2022/0079613 | A1 * | 3/2022 | Aljuri ................ A61B 17/3203 |

FOREIGN PATENT DOCUMENTS

| | | |
|---|---|---|
| CN | 101945621 | 1/2011 |
| CN | 202822454 | 3/2013 |
| EP | 1 420 720 | 9/2007 |
| EP | 1 599 153 | 11/2010 |
| EP | 1 959 876 | 9/2011 |
| EP | 1 827 305 | 1/2012 |
| EP | 2 446 855 | 5/2012 |
| EP | 2 316 392 | 1/2013 |
| EP | 3 167 845 | 5/2017 |
| EP | 3 328 317 | 6/2018 |
| EP | 3 415 121 | 12/2018 |
| EP | 2 685 933 | 2/2019 |
| EP | 3 089 780 | 9/2019 |
| EP | 3 597 148 | 1/2020 |
| EP | 3 610 831 | 2/2020 |
| EP | 3 096 711 | 3/2021 |
| EP | 3 831 342 | 6/2021 |
| FR | 2586185 | 2/1987 |
| JP | 51-51894 | 5/1976 |
| JP | 2005-261686 | 9/2005 |
| WO | WO 90/13332 | 11/1990 |
| WO | WO 2011/021779 | 2/2011 |
| WO | WO 2011/002779 | 6/2011 |
| WO | WO 2015/101975 | 7/2015 |
| WO | WO 2015/111063 | 7/2015 |
| WO | WO 2015/138763 | 9/2015 |
| WO | WO 2017/081326 | 5/2017 |
| WO | WO 2021/099646 | 5/2021 |
| WO | WO 2021/113340 | 6/2021 |

* cited by examiner

IMPLANT DELIVERY METHODS

CROSS-REFERENCE TO RELATED APPLICATIONS

This application is a continuation of U.S. patent application Ser. No. 16/692,347, filed on Nov. 22, 2019 and issued as U.S. Pat. No. 11,273,025 on Mar. 15, 2022, which is hereby incorporated by reference in its entirety.

TECHNICAL FIELD

The present disclosure relates to a delivery device for an expandable implant, in particular but not exclusively, the expandable implant may be located within the prostatic urethra of a patient to treat benign prostatic hyperplasia. Aspects of the invention relate to a delivery device for locating an expandable implant for treating benign prostatic hyperplasia within the prostatic urethra and to a method of delivering an expandable implant.

BACKGROUND

Benign prostatic hyperplasia (BPH) is a noncancerous disease that results in an enlargement of the prostate. As the prostate expands it may press against and place pressure on the urethra and bladder neck thereby making it difficult to pass urine out of the bladder.

It is known to treat BPH in a variety of manners including through the use of medication or surgery in particularly bad cases. However, both of these approaches are undesirable. For example, in the US alone more than $5 billion is spent annually on medication to manage BPH. Furthermore, surgical solutions can be particularly invasive and uncomfortable for the patient.

As such, there is a move in the industry towards the use of expandable implants that may be inserted within the urethra to alleviate the pressure applied to the urethra and bladder neck by the enlarged prostate.

Expandable implants provide a minimally invasive and low cost solution for treating BPH. However, locating the expandable implant in the correct position within the urethra is challenging for a clinician. Furthermore, if the expander is deployed incorrectly it may be challenging and invasive to recover the deployed expander from the patient's body.

An example of an expandable implant for treating BPH is described in WO 2017/081326. The expandable implant described in WO 2017/081326 should be positioned within the prostatic urethra between the bladder neck and external sphincter of a patient such that the expandable implant provides a radially outward force on the prostatic urethra to alleviate the symptoms of BPH.

Positioning the expander accurately within the prostatic urethra is challenging for a clinician as the expander must be positioned accurately both in a longitudinal direction within the prostatic urethra and also circumferentially. For example, the expandable implant should be positioned longitudinally between the bladder neck and the external sphincter and also orientated such that the expander correctly engages the three lobes of the prostate. If the expander is deployed in an incorrect position or deployed accidently then a complex procedure may be required to remove or reposition the expander within the prostatic urethra.

As such, there is a need to provide a minimally invasive delivery device that allows a clinician to accurately position and deploy the expandable implant within the prostatic urethra.

WO 2017/081326 describes a delivery device for delivering an expander to a target site within a body lumen. The delivery device comprises an ejection element with a triangular cross-section configured to engage the expandable implant. The delivery device may be inserted into the urethra through the penis and advanced along the urethra to the target site. When the clinician is satisfied that the expander is in the correct position the ejection element is advanced distally and the expander is ejected from the delivery device.

The problem with this delivery device is that the expander is not reliably and accurately positioned within the prostatic urethra of the patient. For example, advancing the ejection element causes the expander to spring or jump forward upon deployment thereby making it challenging to accurately position the expander both longitudinally and circumferentially within the prostatic urethra. This system relies on the expander to expand and self-locate relative to the anatomy which can be unreliable and unpredictable.

Furthermore, deployment of the expander from the delivery device is achieved by actuating the handle in a single step thereby making the delivery device susceptible to accidental deployment and does not allow the clinician to reverse deployment of the expander if the clinician decides that the expander is not positioned accurately within the target site.

It is an aim of the present invention to address one or more of the disadvantages associated with the prior art.

SUMMARY OF THE INVENTION

In general terms there is provided a delivery device for locating an expandable implant for treating BPH within the prostatic urethra of a patient, the delivery device comprising: an inner tube; and an outer sleeve moveable relative to the inner tube between a stored position and a deployed position; wherein the outer sleeve surrounds the inner tube to define an annulus therebetween and wherein the expandable implant is retained within the annulus when the outer sleeve is in the stored position. The outer sleeve may be moveable between a stored position and a deployed position. The stored position is a position in which the outer sleeve at least partially surrounds the expandable implant such that the implant is retained on the inner tube. When in the stored position the outer sleeve prevents the expandable implant expanding radially. The deployed position is a position in which the expander is uncovered by the outer sleeve such that the outer sleeve may expand radially.

According to an aspect of the present invention there is provided a delivery device for locating an expandable implant for treating BPH within the prostatic urethra of a patient, the delivery device comprising: a first elongate element; and a second elongate element surrounding the first elongate element to define an annulus therebetween; wherein the second elongate element is retractable relative to the first elongate element, between: a stored position in which the second elongate element is configured to surround the implant thereby retaining the implant within the annulus; a partially-deployed position in which the second elongate element is configured to partially uncover the implant; and a fully-deployed position in which the second elongate element is configured to uncover the implant to an extent sufficient to allow the implant to expand radially within the prostatic urethra.

The first elongate element may be, for example, an inner tube or rod and the second elongate element may be an outer sleeve. The first and second elongate elements may be elliptical and preferably cylindrical.

The delivery device beneficially provides a device for accurately positioning and deploying an expandable implant for treating BPH within the prostatic urethra of the patient. The outer sleeve may retain the expandable implant or expander within the annulus by surrounding the expander and preventing radial expansion of the expander until the expander is correctly located within the prostatic urethra. The skilled reader will appreciate that whilst the expandable implant described above is for use in treating BPH the delivery system may be used in other applications in which an expandable implant is to be located within a body lumen.

In an embodiment, when in the partially deployed position a distal tip of the second elongate element may be positioned proximally of a distal tip of the first elongate element. The partially deployed position beneficially uncovers a portion of the expander whilst retaining the expander in a compressed or stored configuration on the inner tube. This allows a clinician to view the expander relative to the anatomy thereby making it easier for a clinician to align the expander relative to the anatomy. Furthermore, moving the outer sleeve from the partially deployed position to the fully deployed position is a smaller longitudinal movement than from the stored to the fully deployed position which improves the accuracy of deployment of the expandable implant.

In one embodiment the delivery device may comprise a third elongate element located between the first elongate element and the second elongate element. The third elongate element may an intermediate tube or a steering tube.

In another embodiment the delivery device may comprise a retention feature for inhibiting movement of the expandable implant. The retention feature advantageously retains the expandable implant relative to the inner tube or the steering tube within the annulus. This is beneficial as it prevents longitudinal or angular movement of the expandable implant relative to the inner tube or steering tube prior to deployment of the expander. In an embodiment the retention feature may be located within the annulus.

In one embodiment the outer sleeve may surround the retention feature when in the partially deployed position or in the stored position. This is beneficial as the outer sleeve prevents radial expansion of the expandable implant prior to full deployment of the expandable implant. Furthermore, the outer sleeve may be returned from the partially deployed position to the stored position if the clinician wants to abort the deployment of the expandable implant.

In an embodiment the retention feature may comprise a protrusion on the inner tube. In another embodiment the retention feature may comprise a proximal protrusion and a distal protrusion located on the inner tube. The inner tube may comprise two, three or more sets of retention features configured to engage and retain the expandable implant. In another embodiment the protrusions may be located on or extending distally from the steering tube. The protrusions may be orientated on the inner tube or steering tube such that the expandable implant is orientated substantially correctly when the delivery device is inserted into the urethra.

In another embodiment a slot for at least partially receiving the expandable implant may be defined between the distal protrusion and the proximal protrusion. The expandable implant may be received within the slot. The expandable implant may comprise an apex and the protrusion may be located between opposing sides of the apex when the expandable implant is located on the inner tube.

In one embodiment a gap may be defined between a top or radially outer surface of the retention feature and an inner or radially inner surface of the outer sleeve when the outer sleeve is in the stored position or in the partially-deployed position, which gap is narrower than a radial thickness of a part of the implant to be engaged by the retention feature. In an embodiment the delivery device may comprise the expander and the implant or expander may comprise a wire retained by the retention feature and the gap may be less than the diameter of the wire. The gap beneficially provides clearance between the retention feature and the outer sleeve to allow the outer sleeve to move freely relative to the inner tube. Furthermore, the gap may allow fluids to flow along the annulus if the annulus forms part of an irrigation channel.

In another embodiment the delivery device may comprise a handle connected to a proximal end of the inner tube and/or outer sleeve. The handle advantageously allows the delivery device to be held and gripped by a clinician. Furthermore, the handle may be operable to move the outer sleeve between a stored position, a fully deployed position and a partially deployed position.

In an embodiment the handle may comprise a proximal grip and a distal grip. The handle may comprise a lever moveable between a locked position and an unlocked position. When the lever is in the locked position the outer sleeve is locked in the stored position. The lever may comprise an intermediate position and when the lever is in the intermediate position the outer sleeve is moveable from the stored position to the partially deployed position.

The lever may comprise a fully deployed position. When the lever is in the fully deployed position the outer sleeve is moveable between the partially deployed position and the fully deployed position.

In one embodiment the inner tube may comprise a distal end and the distal end of the inner tube may be located distally of a distal end of the expandable implant when the expandable implant is retained within the annulus, in use.

In another embodiment the inner tube may comprise a distal end and the distal end may be located proximally of a distal end of the expandable implant and distally of a proximal end of the expandable implant when the expandable implant is retained within the annulus, in use.

Beneficially, the inner tube provides support to the expandable implant when the expandable implant is retained on the inner tube such that the longitudinal struts of the expandable implant are maintained in a generally parallel orientation relative to each other when the implant is in the stored configuration. This advantageously promotes radial expansion of the implant during deployment and further reduces the possibility of the expandable implant becoming dislodged from the retention feature. Furthermore, the inner tube supports the expander when the delivery tube is being inserted into, and along, the urethra. This beneficially prevents the expander being compressed further by the urethra as this may cause the expander to disengage the retention features.

In an embodiment the inner tube may comprise an inner lumen. The inner lumen may run along the length of the inner tube. Furthermore, the inner lumen may act as an irrigation channel for clearing the field of view and draining fluids from the bladder and or urethra. In one embodiment the delivery device may comprise an imaging device at least partially received within the inner lumen. In an embodiment the inner tube may be an imaging device. The imaging device may comprise an imaging chip or the imaging device may be a telescope. The imaging chip may be connected to an image display device and the wires connecting the imaging device to the image display device and power module may run through the inner lumen.

The field of view of the imaging device may include at least a portion of the expander when the expander is in the stored configuration on the inner tube. This is beneficial as the imaging device may generate images of the expander relative to the anatomy of the patient. This allows the clinician to accurately locate and position the expandable implant relative to the anatomy by using the images from the imaging device.

In an embodiment the imaging device may be moveable relative to the inner tube and may be fixed relative to the outer sleeve. As such, the imaging device may be moved relative to the inner tube when the outer sleeve is moved between the stored, partially deployed and fully deployed positions.

In another embodiment the inner tube, optionally the imaging device, is moveable longitudinally relative to the steering tube between a distally advanced position and a proximally retracted position. A distal tip of the inner tube may be positioned distally with respect to the distal tip of the outer sleeve when the inner tube is in the distally advanced position. The outer sleeve may be outside a field of view of the imaging device when the first elongate element is in the distally advanced position. The imaging device may be configured such that its field of view captures at least a distal portion of the implant when the inner tube is in the proximally retracted position.

In an embodiment the outer sleeve may comprise graduation marks spaced at intervals. The graduation marks beneficially provide a visual aid to the clinician when positioning the expander 10 in the desired longitudinal position. The graduation marks may be on the inner tube if the outer sleeve is transparent such that the graduation marks are visible to the clinician.

In an embodiment the delivery device may comprise an expandable implant. The expandable implant may be supported by the first elongate element and at least partially covered by the second elongate element.

A method of deploying an expandable implant within a patient's urethra, the method comprising: inserting a delivery tube into the urethra with the implant retained within and covered by the delivery tube; retracting the delivery tube proximally, relative to the implant, to a partially-retracted position in which the implant is at least partially uncovered while still being retained by the delivery tube; positioning the implant at a target site within the urethra; and deploying the implant at the target site by further retracting the delivery tube to an extent sufficient to release the implant from the delivery tube.

Deploying the expander in a two-stage deployment process beneficially reduces the likelihood of the clinician deploying the expandable implant incorrectly. Furthermore, the partially deployed position allows the expandable implant to be aligned with the anatomy when it is partially uncovered. Inserting the delivery tube when the implant is covered by the outer sleeve is beneficial as it allows the delivery device to be easily inserted into the urethra without the expandable implant potentially catching on the anatomy.

In one embodiment the method may comprise positioning the implant at the target site at a longitudinal position in the urethra between the patient's bladder neck and external sphincter. The method may comprise advancing a distal end of the delivery tube distally along the urethra to, or distally beyond, the bladder neck. This is beneficial as the anatomy along the length of the urethra may be viewed as the delivery device is advanced along the urethra. This allows the clinician to check for any obstructions within the urethra and to view the prostatic lobes.

In an embodiment the method may comprise pulling the distal end of the delivery tube back from the bladder neck in a proximal direction. The bladder neck may be used as a datum for positioning the expandable implant in the longitudinal position. The delivery device may be advanced into the bladder. The delivery tube may comprise of graduation marks with which to position the expandable implant in a clinically acceptable position from the bladder neck datum prior to deployment.

In another embodiment positioning the expandable implant comprises rotating the implant about a longitudinal axis of the delivery tube when positioning the implant at the target site. The implant may be rotated to align the implant with at least one prostatic lobe of the patient. In an embodiment the implant may comprise at least one apex and the implant may be rotated to align the at least one apex with the prostatic lobe. The expander may be secured relative to the delivery device such that rotating the delivery device rotates the expander. The method may comprise aligning at least one apex of the implant with the or each prostatic lobe.

In one embodiment the delivery tube may comprise an inner tube and the inner tube is static relative to the urethra when the delivery tube is moved from the partially deployed configuration to the fully deployed configuration. The method may comprise holding the implant substantially stationary relative to the urethra when further retracting the delivery tube from the partially deployed to the fully deployed position. This is beneficial as the expandable implant may be secured to the inner tube when in the partially deployed configuration and thus the expander may remain in a substantially unchanged longitudinal position when the delivery device is moved to the fully deployed configuration. This is beneficial as it improves the accuracy of the deployment of the expandable implant from the stored position to the deployed position within the prostatic urethra.

In one embodiment deploying the expandable implant may comprise expanding the implant radially. The expandable implant may be expanded radially from stored or compressed position to an expanded position. The expandable implant may be deployed by moving an outer sleeve longitudinally relative to the expandable implant. The expandable implant may be unsheathed or uncovered to allow the expandable implant to expand radially.

In another embodiment moving the delivery tube to the partially deployed configuration may comprise operating a safety catch to enable the delivery tube to be moved or reconfigured. The method may further comprise moving the safety catch to a further position to enable the delivery tube to be further retracted from the partially-retracted position.

In one embodiment the method may comprise retaining the implant by engagement with retaining formations that remain covered by the delivery tube in the partially-retracted position but that are exposed by said further retraction of the delivery tube to release the implant. The method may comprise advancing the delivery tube distally to cover the retaining formations before removing the delivery tube from the urethra.

The method may comprise viewing the implant relative to the urethra from a viewpoint within the implant and disposed proximally relative to a distal end of the implant, when the delivery tube in the partially-retracted position.

In an embodiment the method may comprise aligning at least one apex of the implant with the patient's verumontanum. The method may comprise locating the verumontanum between laterally-spaced longitudinally extending members of the implant. The method may comprise pulling back the implant proximally while avoiding contact of the apex with the verumontanum. The method may further comprise steering the delivery tube by bending at least a distal portion of the delivery tube along its length.

In an embodiment the method may comprise moving the delivery tube from the fully deployed configuration to the stored configuration prior to removing the delivery tube from the urethra.

In an embodiment the method may comprise viewing the expander relative to the urethra.

Alternatively presented, the invention is a delivery device for locating an expandable implant within the prostatic urethra of a patient for treating BPH, the delivery device comprising: a first elongate element; and a second elongate element surrounding the first elongate element to define an annulus therebetween; wherein the second elongate element is retractable relative to the first elongate element, between: a stored position in which the second elongate element is configured to surround the implant thereby retaining the implant within the annulus; a partial-deployment position in which the second elongate element is configured to partially uncover the implant; and a full-deployment position in which the second elongate element is configured to uncover the implant to an extent sufficient to release the implant for radial expansion within the prostatic urethra. Furthermore, wherein when in the partially deployed position a distal tip of the second elongate element is positioned proximally relative to a distal tip of the first elongate element; further comprising a third elongate element disposed between the first elongate element and the second elongate element; further comprising at least one retention feature for inhibiting movement of the implant; wherein the retention feature is located within the annulus; wherein the retention feature comprises at least one protrusion; wherein the retention feature comprises a proximal protrusion and a distal protrusion; wherein a slot for at least partially receiving the expandable implant is defined between the distal protrusion and the proximal protrusion; wherein the second elongate element surrounds the retention feature when in the partial-deployment position and in the stored position; wherein a gap is defined between a radially outer surface of the retention feature and a radially inner surface of the second elongate element when the second elongate element is in the stored position and in the partial-deployment position, which gap is narrower than a radial thickness of a part of the implant to be engaged by the retention feature; wherein the retention feature is located on the first elongate element; wherein the retention feature is located on the third elongate element; wherein the first elongate element comprises a groove for at least partially receiving the retention feature; further comprising a handle connected to a proximal end of the first elongate element and/or the second elongate element; wherein the handle comprises a proximal grip and a distal grip; wherein the handle is operable to move the second elongate element between the stored position, the partial-deployment position and the full-deployment position; wherein the handle comprises a lever moveable between a locked position and an unlocked position, the second elongate element being locked in the stored position when the lever is in the locked position; wherein the second elongate element is moveable from the stored position to the partial-deployment position when the lever is in an intermediate position; wherein a distal end of the first elongate element is configured to be located distally of a distal end of the implant when the implant is retained within the annulus, in use; wherein the first elongate element comprises an imaging device; wherein the first elongate element comprises an inner lumen and wherein a telescope is at least partially received within the inner lumen; wherein the telescope is moveable relative to the first elongate element and is fixed relative to the second elongate element to be moved relative to the first elongate element when the second elongate element is moved between the stored, partial-deployment and full-deployment positions; wherein the first elongate element is moveable longitudinally relative to the third elongate element between a distally advanced position and a proximally retracted position; wherein a distal tip of the first elongate element is positioned distally with respect to the distal tip of the second elongate element when the first elongate element is in the distally advanced position; wherein the second elongate element is outside a field of view of the imaging device when the first elongate element is in the distally advanced position; wherein the imaging device is configured such that its field of view captures at least a distal portion of the implant when the first elongate element is in the proximally retracted position; wherein the first elongate element is an inner rod and the second elongate element is an outer sleeve; wherein the third elongate element comprises a steering tube; and/or in combination with an expandable implant that is supported by the first elongate element and is at least partially covered by the second elongate element.

BRIEF DESCRIPTION OF THE DRAWINGS

One or more embodiments of the invention will now be described, by way of example only, with reference to the accompanying drawings, in which.

DETAILED DESCRIPTION

In general terms embodiments of the invention relate to a delivery device for deploying an expandable implant within the prostatic urethra of a patient to alleviate the symptoms of BPH. In a broad sense the delivery device comprises a handle operatively connected to an elongate delivery tube. The delivery tube comprises an inner tube surrounded by an outer sleeve or sheath with an annulus defined therebetween. The expandable implant may be retained in a compressed or stored configuration within the annulus. The inner tube comprises a retention feature positioned at the distal end region of the inner tube for retaining the expander in a compressed or stored configuration within the annulus relative to the inner tube.

The delivery tube may be inserted into the urethra of the patient through the penis and advanced along the urethra to the prostatic urethra. When the clinician is satisfied that the distal end portion, and thus the expander, is accurately positioned within the prostatic urethra the clinician may operate the handle to retract the outer sheath thereby allowing the expander to expand and deploy within the prostatic urethra of the patient.

Deployment of the expander from the delivery device may be a two-stage process in which the outer sheath is first retracted to a partially deployed position. In the partially deployed position the expander is at least partially unsheathed but remains attached to the delivery device. If the clinician is satisfied that the expander is located correctly the outer sheath may be moved to the fully deployed position to release the expander from the delivery device thereby locating the device at the target site within the body lumen, for example the prostatic urethra.

The delivery device advantageously allows the expandable implant to be accurately positioned within the anatomy prior to being deployed within the prostatic urethra in a controlled manner. The controlled deployment of the expander beneficially prevents the expander being inadvertently deployed by a clinician and ensures that the expander is accurately positioned within the prostatic urethra after deployment.

Figure 1:
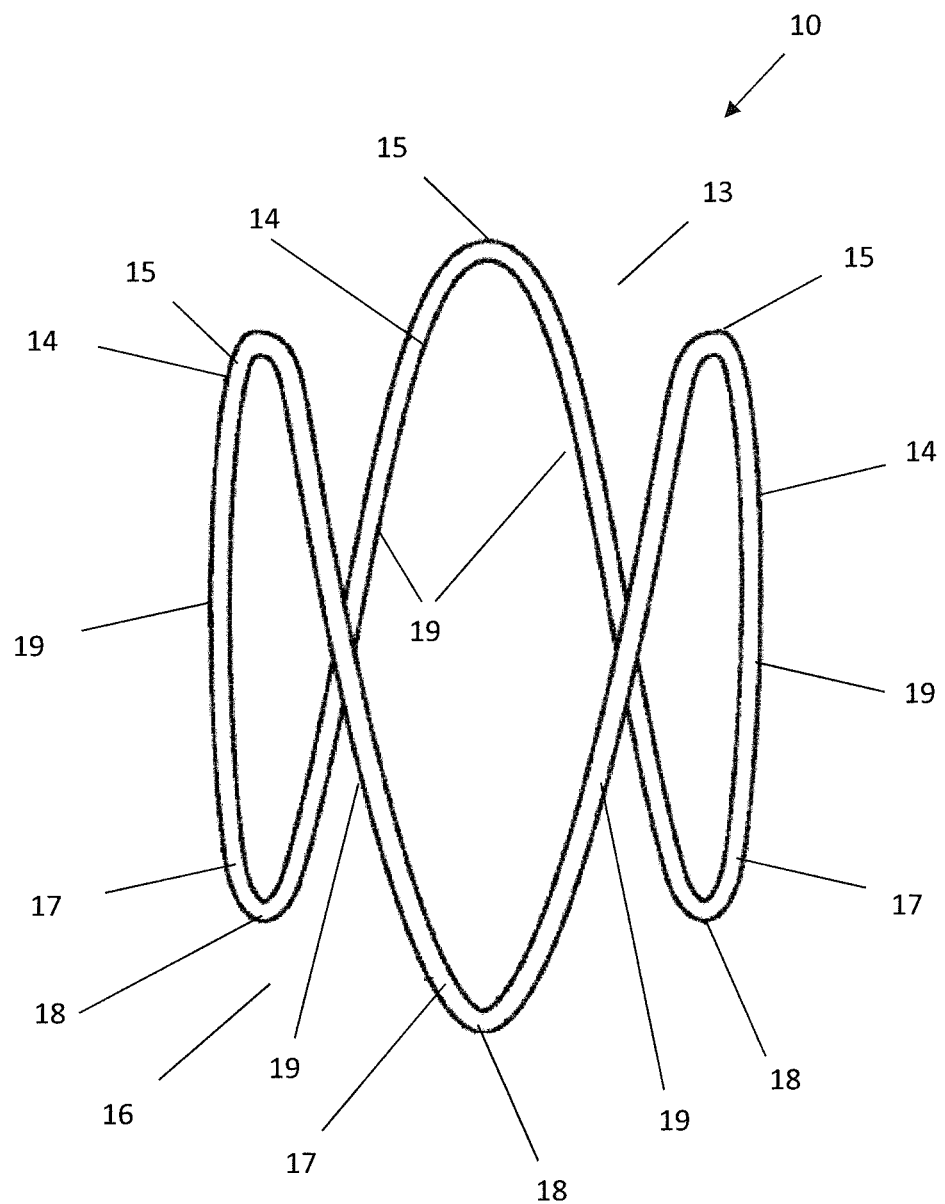
FIG. 1 is a perspective view of an expander in an expanded state suitable for use with embodiments of the invention.
Figure 2:
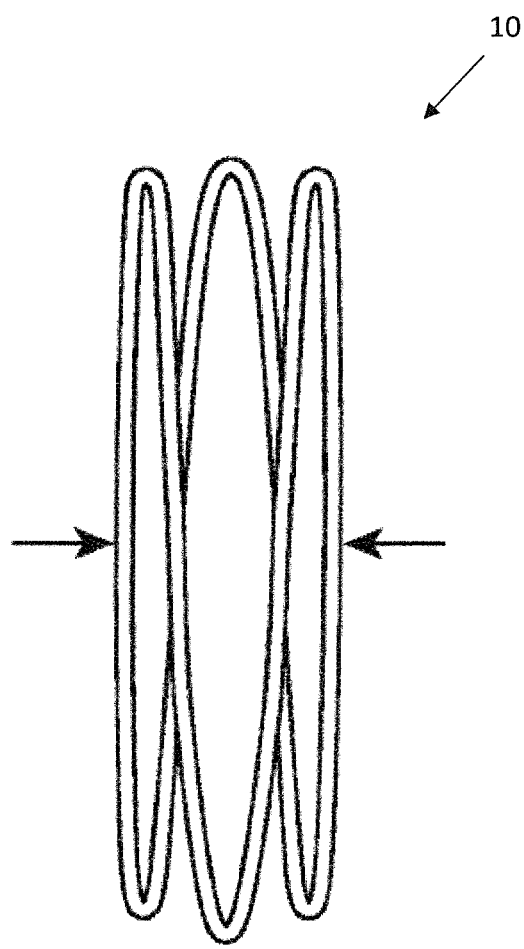
FIG. 2 is a perspective view of the expander of FIG. 1 in a stored state.

To place embodiments of the invention in a suitable context reference will firstly be made to FIG. 1 which shows a schematic diagram of an expandable implant or expander 10 suitable for use with embodiments of the present invention. The expander 10 comprises a single nitinol wire arranged to form a sinusoidal ring. The expander 10 is moveable between an expanded or deployed state as shown in FIG. 1 and a compressed or stowed state as shown in FIG. 2. The nitinol wire ring of the expander 10 acts with superelastic shape memory properties such that when in the compressed state the expander 10 exerts an outward radial force urging the expander 10 to the expanded state. The skilled reader will understand that the expander 10 shown in FIG. 1 is by way of example only and the delivery device described herein may be suitable for use with other expanders.

The expander 10 comprises a proximal end 16 comprising three proximal prongs 17 with apices 18 and a distal end 13 comprising three distal prongs 14 with apices 15. The distal end 13 and proximal end 16 are joined by longitudinal struts 19.

Turning now to FIG. 2, the expander 10 is shown in a contracted or compressed state. When in the contracted state the diameter of the sinusoidal ring defined by the expander 10 is reduced such that the expander 10 may be advanced along the urethra of a patient with minimal discomfort. The expander 10 is delivered to the prostatic urethra 30 in the contracted or delivery state.

Figure 3:
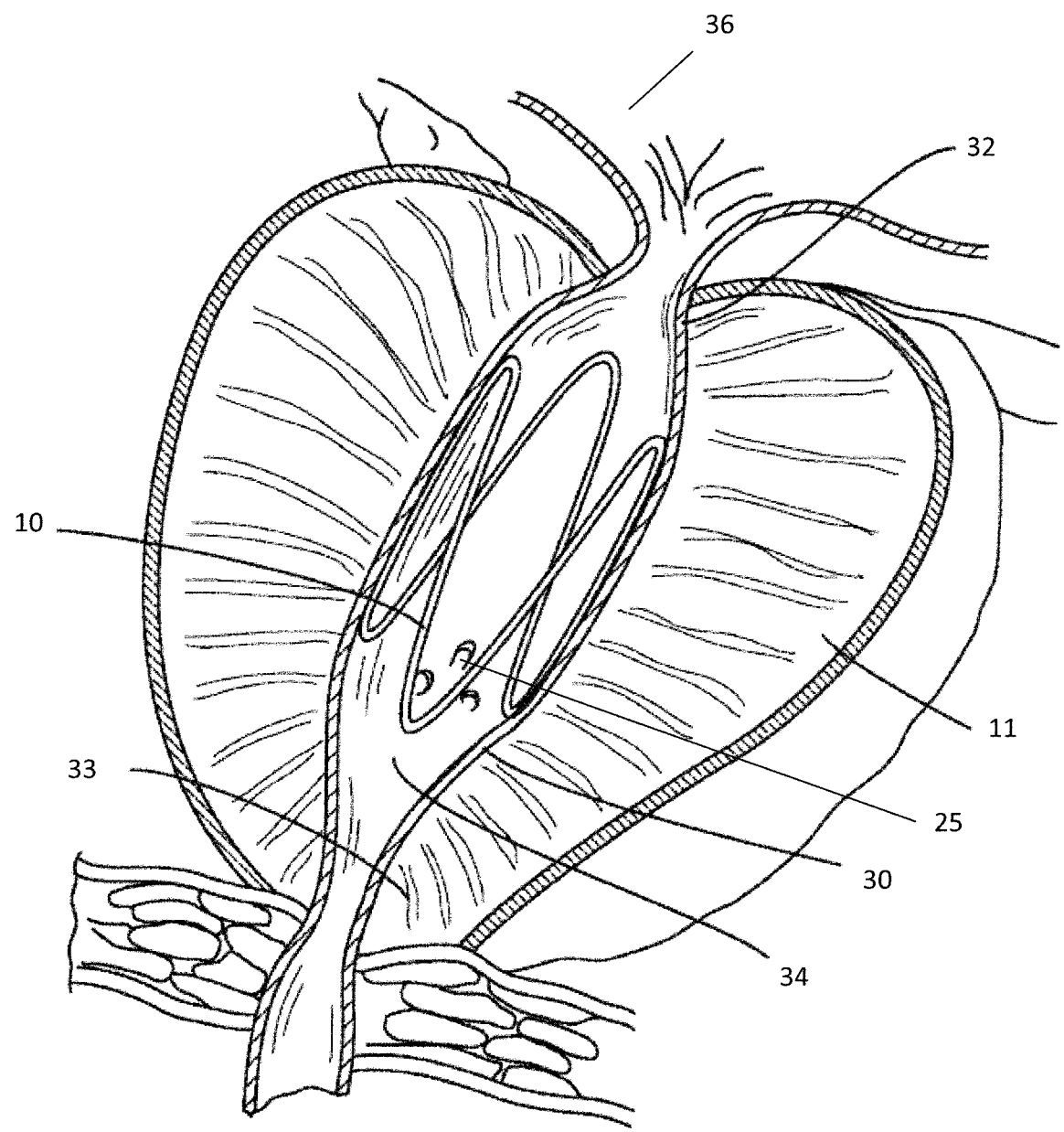
FIG. 3 is a cross-sectional view of a prostate and prostatic urethra with the expander of FIG. 1 in use for the treatment of BPH.

Referring now to FIG. 3, the expander 10 is shown in use in the treatment of benign prostatic hyperplasia (BPH) within the prostate 11. In use, the expander 10 is located within the prostatic urethra 30 between the bladder neck 32 and the external sphincter 33. When the expander 10 is located in this position the expander 10 exerts an outward radial force against the walls of the prostatic urethra 30 to permit the flow of urine from the bladder 36.

Positioning the expander 10 longitudinally between the bladder neck 32 and the external sphincter 33 is challenging and care should be taken to ensure that the expander 10 is suitably positioned prior to deployment. Positioning the expander 10 too close to either the bladder neck 32 or external sphincter 33 is undesirable as the muscle action of the sphincters may cause the expander 10 to migrate over time.

As shown in FIG. 3, the expander 10 is orientated angularly such that the verumontanum 25 and seminal ducts 34 are unobstructed by the expander 10 thereby preserving the sexual function of the patient. Furthermore, the longitudinal struts 19 of the expander 10 are orientate to engage each lobe of the prostate 11 thereby exerting an outward radial force on each lobe to maintain an open passage between the bladder neck 32 and the external sphincter 33.

Figure 4:
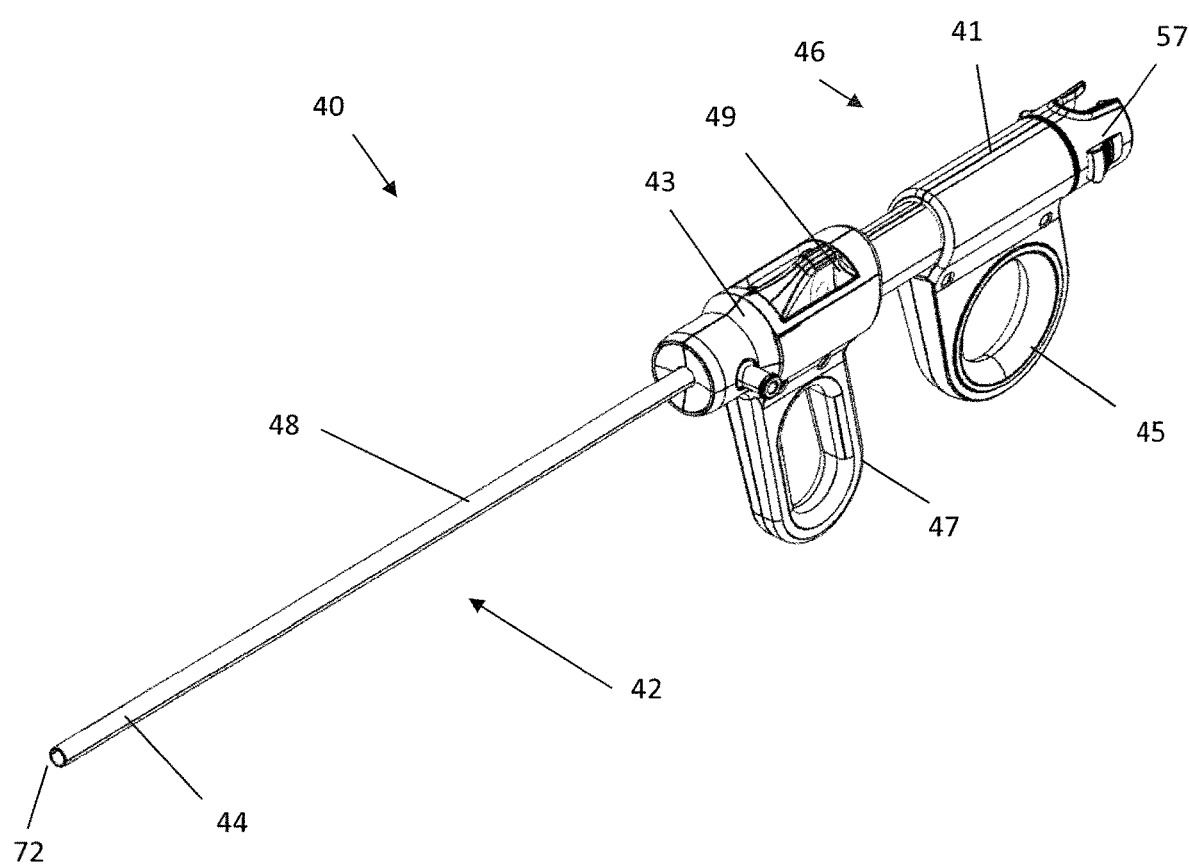
FIG. 4 is a perspective view of a delivery device according to an embodiment of the invention.

Turning now to FIG. 4, a delivery device 40 for positioning the expander 10 within the prostatic urethra 30 is shown. The delivery device 40 comprises a handle 46 operatively connected to an elongate delivery tube 42. The delivery tube 42 is configured to at least partially receive the expander 10 in a compressed state and to deploy the expander 10 within the prostatic urethra 30 of a patient. The delivery tube 42 may be inserted into the urethra of the patient via the penis and advanced along the urethra to a target site, for example the prostatic urethra 30, where the expander 10 may be deployed.

Figure 5:
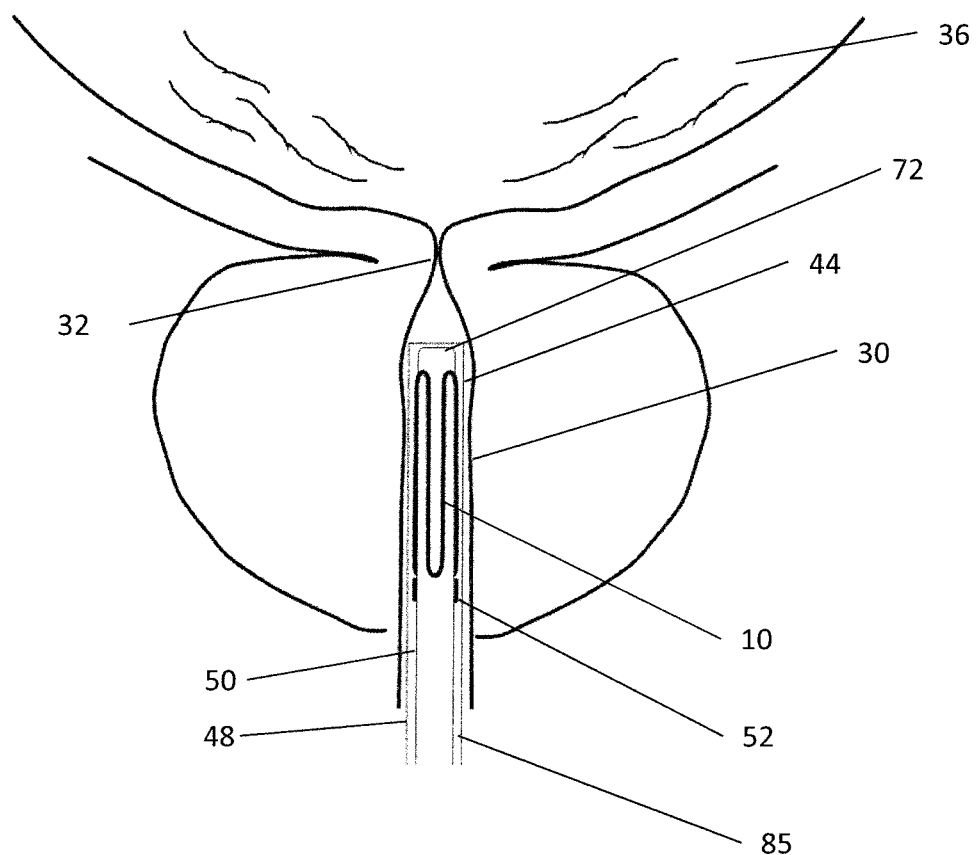
FIG. 5 is a schematic view of the distal end of the delivery device of FIG. 4 positioned within the prostatic urethra of a patient.

FIG. 5 shows a schematic view of the distal end portion 44 of the delivery tube 42 located within the prostatic urethra 30. As shown in FIG. 5, the delivery tube 42 comprises an inner tube 50 that is surrounded by an outer sleeve 48. An annulus 85 is defined between the inner tube 50 and the outer sleeve 48 and the expander 10 is located within the annulus 85. The outer sleeve 48 surrounds the expander 10 thereby preventing the expander 10 from expanding from the stored configuration to the deployed configuration. The annulus 85 serves to retain the expander 10 at the distal end region 44 of the delivery tube 42 and further acts as an irrigation channel along which fluids may be irrigated to or from the urethra and/or bladder 36.

The handle 46 is operatively coupled to the delivery tube 42 such that operating the handle 46 allows a clinician to move the outer sleeve 48 longitudinally relative to the inner tube 50. The lumen 70 on the inner tube 50 may extend through the handle 46 and terminate at a proximal end of the handle 46 in a telescope plug 57 suitable for receiving an imaging device, such as a telescope. The plug 57 may be configured to retain a telescope within the inner lumen 70 such that the telescope may provide images from the distal end 44 of the delivery tube 42. Beneficially, the plug 57 is positioned on the proximal handle 41 which is connected to the inner tube 50 and outer tube 48 and as such the telescope is fixed relative to the outer tube 48 and always moves with in such that the telescope moved longitudinally relative to the inner tube 50 when the clinician operates the handle 46. The plug 57 advantageously provides a datum against which the position of the expander 10 may be measured in relation to the telescope distal tip and outer sleeve 48.

The outer sleeve 48 is moveable between a sheathing or stored position in which the expander 10 is surrounded by the outer sleeve 48 along its length (as shown in FIG. 5) and a deployed or retracted position in which the outer sleeve 48 is moved proximally relative to the inner tube 50 to uncover the expander 10 within the delivery tube 42. Furthermore, the outer sleeve 48 is moveable to an intermediate or partially deployed position in which the expander 10 is partially uncovered but retained on the inner tube 50 as is described in further detail below.

The inner tube 50 comprises retention formations 52 for preventing longitudinal or angular movement of the expander 10 relative to the inner tube 50 when the expander 10 is being retained in the stored configuration within the delivery tube 42. The retention formations 52 are positioned at the proximal end 16 of the expander 10 at a longitudinal position such that the entire expander 10 is retained within the outer sleeve 48 at the distal end portion 44 of the delivery tube 42 when the outer sleeve 48 is in the stored configuration.

FIG. 5 shows an embodiment wherein the distal end 44 of the inner tube 50 extends along the longitudinal length of the expander 10 such that the expander 10 is supported along its entire length by the inner tube 50. In another embodiment the distal tip 72 of the inner tube 50 may extend distally from the retention formations 52 part way along the length of the expander 10. Supporting the expander 10 along its length is beneficial when the expander 10 is being advanced along the urethra as it prevents the expander 10 deforming and potentially disengaging the retention formations 52.

Figure 6:
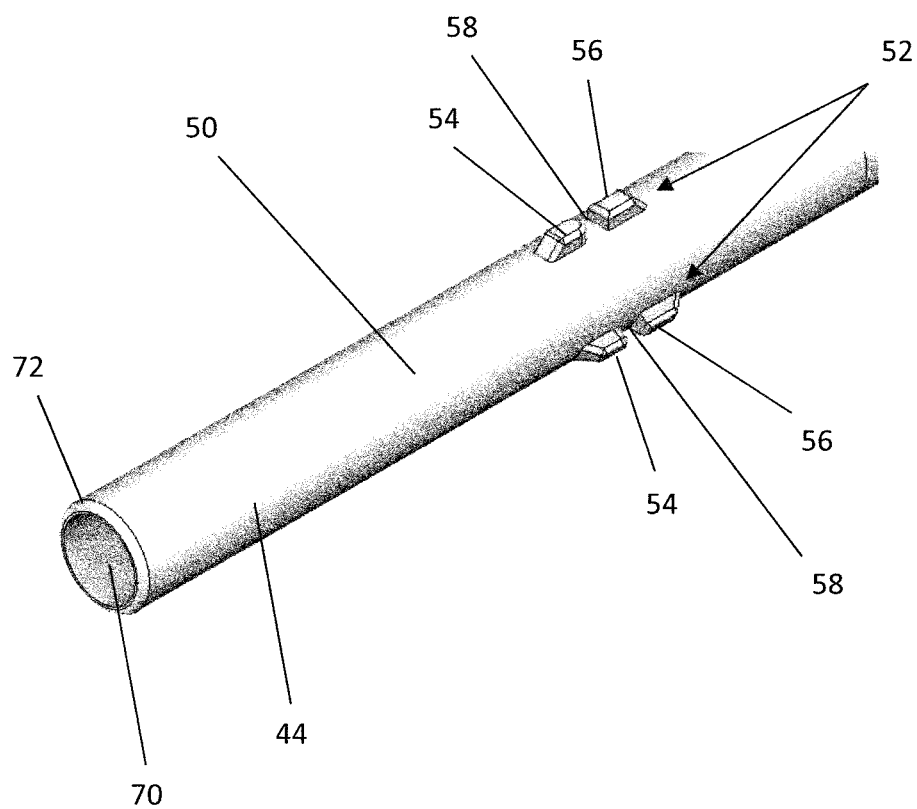
FIG. 6 is a perspective view of an underside of the distal end of the inner tube of the delivery device of FIG. 4.

Turning now to FIG. 6 a perspective view of the underside of the distal end portion 44 of the inner tube 50 is shown with the outer sleeve 50 and imaging device removed for clarity. The inner tube 50 is an elongate plastics tube comprising a distal end portion 44 and a proximal end coupled to the handle 46. The inner tube 50 comprises a hollow inner lumen 70 that may be used to receive the imaging device, for example the telescope or an imaging chip.

Figure 7:
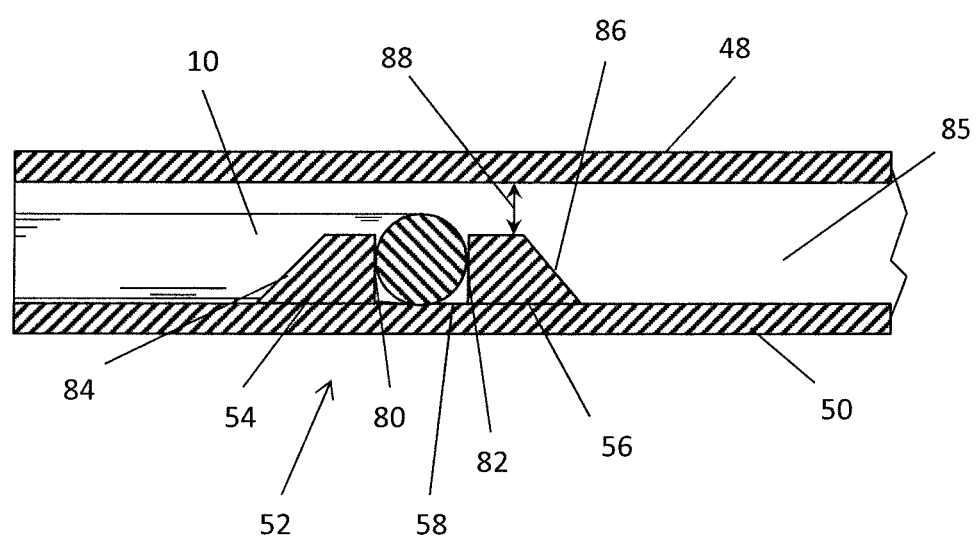
FIG. 7 is a longitudinal sectional view of a retention formation and expander on the inner tube of FIG. 6.
Figure 8:
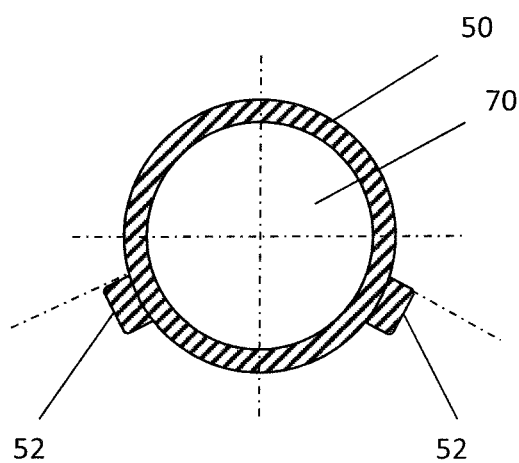
FIG. 8 is a cross-sectional view of the distal end of the inner tube of FIG. 6.

As shown in FIGS. 6 to 8, the inner tube 50 comprises two sets of retention formations 52. The retention formations 52 are configured to prevent longitudinal or rotational movement of the expander 10 relative to the inner tube 50. The retention formations 52 are located within the distal end portion 44 of the inner tube 50. Typically, the retention formations 52 are positioned on the inner tube 50 at a position proximal of the distal tip 72 by a distance in excess of the length of the expander 10. This is beneficial as when the expander 10 is in the stored position the inner tube 50 may provide an orifice for visualisation of the expander with the anatomy with a telescope and support to the expander 10 along the entire length of the expander 10. This maintains the longitudinal struts 19 generally parallel to each other when in the stored position thus promoting smooth deployment of the expander 10 from the stored position to the expanded position.

Alternatively, when the inner tube 50 is shorter than the outer sleeve 48 such that the outer sleeve 48 overhangs the inner tube 50 the retention formations 52 may be located such that the distal end 13 of the expander 10 also overhangs the distal end of the inner tube 50. In this embodiment the inner tube 50 only provides support to a portion of the expander 10. However, the support provided by the inner tube 50 is sufficient to maintain the longitudinal struts 19 generally parallel to each other when the expander 10 is in the stored configuration.

The retention formations 52 each comprise a distal protrusion 54 and a proximal protrusion 56 that define a retention slot 58 therebetween. The slot 58 is configured to receive a proximal apex 18 of the expander 10 to retain the expander 10 on the inner tube 50. When the expander 10 is located on the inner tube 50 in the compressed configuration the proximal prong 17 of the expander 10 wraps around and engages the distal protrusion 54 of the retention formation 52. This inhibits longitudinal movement of the expander 10 in the distal direction and also rotational movement of the expander 10 relative to the inner tube 50. The proximal apex 18 may abut the proximal protrusion 56 thereby inhibiting movement of the expander 10 longitudinally in the proximal direction.

FIG. 7 shows a longitudinal sectional view of a retention formation 52 with the expander 10 in the stored configuration and surrounded by the outer sleeve 48. The retention formation 52 prevents longitudinal or rotational movement of the expander 10 relative to the inner tube 50. As shown in FIG. 7, the outer sleeve 48 of the delivery device 40 surrounds the expander 10 thereby preventing radially outward expansion of the expander 10 to the deployed position. FIG. 7 shows the outer sleeve 48 in a stored or partially deployed position in which the expander 10 is encircled at least in the region of the retention formations 52 thereby retaining the expander 10 in the stored configuration on the inner tube 50.

The distal protrusion 54 and a proximal protrusion 56 of the retention feature 52 are shown in detail in FIG. 7. The protrusions 54, 56 each comprise a ramped wall 84, 86 such that the retention feature 52 has ramped walls 84, 86 on the distal and proximal side of the retention feature 52.

The ramped walls 84, 86 of the protrusions 54, 56 are designed to minimise the potential for the retention features 52 to re-engage or catch on the expander 10 once the expander 10 has been deployed within the prostatic urethra 30. The ramped walls 84, 86 are positioned on a distal and proximal side of the retention feature 52. As such, if the inner tube 50 is moved longitudinally relative to the deployed expander 10 when the outer sleeve 48 is in the deployed position the ramped surfaces 84, 86 may contact the expander 10 but are unlikely to catch or snag on the deployed expander 10. This is advantageous as catching or snagging the expander 10 once it is deployed may cause the expander 10 to move longitudinally within the anatomy which may result in the expander 10 being positioned incorrectly.

Furthermore, the proximal protrusion 56 and distal protrusion 54 comprises generally vertical walls 80, 82 that define the walls of the slot 58 such that the slot 58 has a U-shaped profile. The vertical walls 80, 82 of the protrusions 54, 56 advantageously act as a guide to the expander 10 when the expander 10 is deployed. The walls 80, 82 promote radial expansion of the expander 10 when the expander 10 is deployed thereby minimising longitudinal movement of the expander 10 relative to the inner tube 50 during deployment.

The slot 58 defined by the distal protrusion 54 and the proximal protrusion 56 may be dimensioned to have a clearance fit with the wire of the expander 10. In another embodiment, the slot 58 may have an interference fit with the wire of the expander 10 such that the slot 58 applies a retaining force on the expander 10. However, the retaining force applied by the slot 58 should be less than the radial outward force of the expander 10 such that the expander 10 may still be deployed when the outer sleeve 48 is pulled back to the deployed position.

As shown in FIG. 7, a gap 88 is created in the annulus 85 between the top surfaces of the protrusions 54, 56 and the inner surface of the outer sleeve 48. The magnitude of the gap 88 is less than the diameter of the wire material of the expander 10 such that the expander 10 is retained within the slot 58 when the outer sleeve 48 is in the stowed position. For example, the gap 88 may be between about 1 mm and 2 mm in height. The expander 10 may contact the inner surface of the outer sleeve 48 when the expander 10 is being retained in the stored position by the outer sleeve 48 and retention formations 52.

FIG. 8 shows a cross-sectional view of the inner tube 50 and the retention formations 52. As shown in FIG. 8 the inner tube 50 comprises two retention formations 52 for retaining the expander 10 on the inner tube 50. The retention formations 52 are spaced angularly by about 120° such that the retention formations 52 may engage two of the proximal prongs 17 of the expander 10. The skilled reader will understand that the retention formations 52 may be spaced angularly by any angle suitable for engaging and retaining an expander on the inner tube 50. Furthermore the skilled reader will understand that the inner tube 50 may comprise two or more retention formations 52 to engage and retain the expander 10.

The retention formations 52 are positioned angularly on the inner tube 50 such that when the delivery tube 42 is inserted into the urethra with the handle 46 in an ergonomic, generally upright position, the expander 10 is orientated to engage the lobes of the prostate 11. This is beneficial as it means the clinician is only required to make relatively small adjustments to the angular position of the expander 10 when positioning the expander within prostatic urethra 30. Furthermore, during deployment of the expander 10 the anterior prostatic urethra may contact and press on the top surface of the inner tube 50 and as such could prevent the expander disengaging the retention feature 52 if a retention feature is positioned on the top surface of the inner tube 50.

Figure 9:
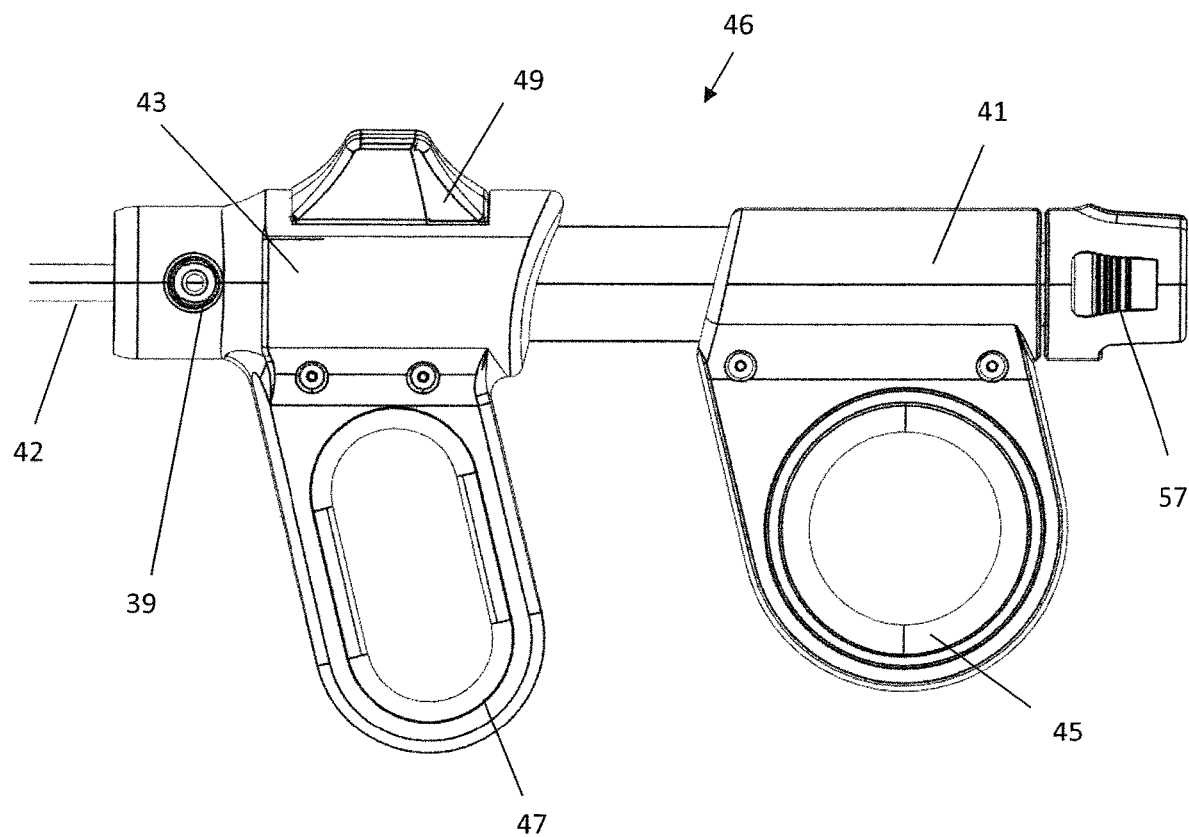
FIG. 9 is a schematic side view of a handle of the delivery device of FIG. 4.

FIG. 9 is a side view of the handle 46 of the delivery device 40. The handle 46 is connected to the proximal end of the delivery tube 42 such that the handle 46 may be held by a clinician and used to position the delivery tube 42. Furthermore, the handle 46 is operable to control the position of the outer sleeve 48 relative to the inner tube 50 such that the outer sleeve 48 may be moved between the stored position, the partially deployed position and the fully deployed position thereby allowing a clinician to deploy the expander 10 by operating the handle 46.

The handle 46 further comprises an irrigation duct 39 that is fluidly connected to the annulus 85 of the delivery tube 42. An irrigation reservoir may be coupled to the irrigation duct 39 such that fluid may be circulated via the annulus 85 to clear the field of view of the imaging device 90 if debris or blood obscures or blocks the field of view of the imaging device. The irrigation duct 39 can also be connected to a vacuum such that the annulus 85 can be used to drain fluid from the bladder 36 and/or urethra to a waste reservoir (not shown).

The handle 46 is designed to be operable by the clinician using a single hand. As such, the handle 46 comprises a proximal grip 41 and a distal grip 43 that are moveable longitudinally relative to each other. Moving the proximal grip 41 relative to the distal grip 43 causes the outer sleeve 48 and telescope to move longitudinally relative to the inner tube 50. The proximal grip 41 may be connected to the inner tube 50 and the distal grip 43 may be connected to the outer sleeve 48 and telescope through the plug 57. As such, moving the grips 41, 43 relative to each other affects relative movement of the inner tube 50 and the outer sleeve and telescope plug 57.

The proximal grip 41 comprises a thumb ring 45 into which the clinician may place their thumb and the distal grip 43 comprises a finger loop 47 into which the clinician may place their fingers. The finger loop 47 allows the clinician to pull the distal grip 43 toward the proximal grip 41 thereby moving the outer sleeve 48 and telescope plug 57 proximally relative to the inner lumen 50. Moving the outer sleeve 48 and telescope plug 57 proximally to the inner lumen 50 is beneficial as it ensures the inner tube 50 and thus the expander 50 is static with respect to the prostatic urethra 30 during deployment and allows the telescope and outer sleeve 48 to move together. This is advantageous as it allows the clinician to deploy the expander 10 in the desired location within the anatomy. Furthermore, the clinician may push their fingers against the distal side of the finger loop 47, opening the hand span and in turn moving the distal grip 43 distally relative to the proximal grip 41. This is beneficial as it allows the clinician to move the outer sleeve 48 from the fully deployed or partially deployed position to the stored position.

The handle 46 further comprises a safety catch or lever 49 located on a top surface of the distal grip 43. The lever 49 is operable to prevent movement of the proximal grip 41 and distal grip 43 relative to each other longitudinally. The lever 49 may be moveable between three distinct positions that correspond to the stored, partially deployed and fully deployed positions of the outer sleeve 48.

Figure 10:
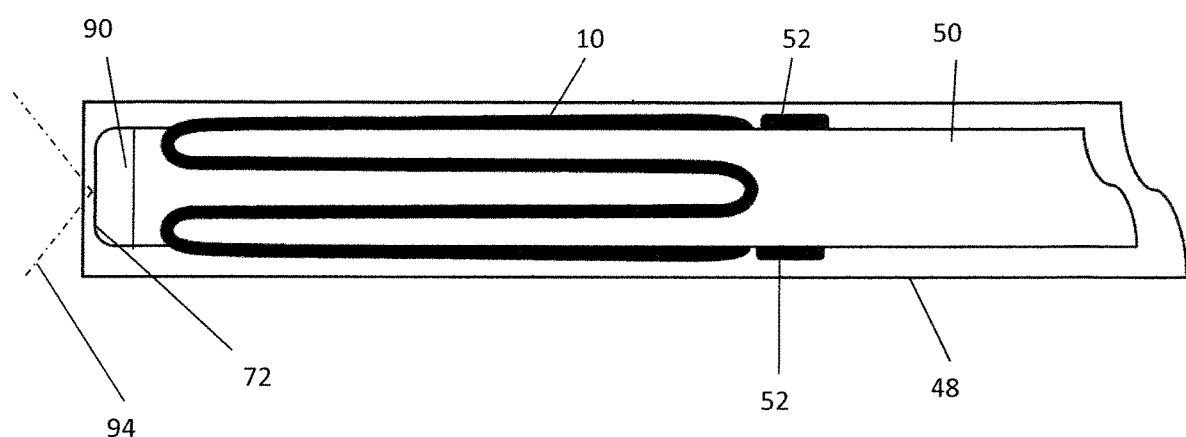
FIG. 10 is a schematic side view of the distal end region of the delivery tube and expander in a stored configuration.

For example, when the lever 49 is in the first, stored, position the proximal grip 41 and distal grip 43 are locked longitudinally relative to each other such that the outer sleeve 48 is retained in the stored position as shown in FIG. 10. This is beneficial as the delivery tube 42 may be inserted within the urethra via the penis by the clinician without the risk of the outer sleeve 48 being moved to the deployed position as doing so would cause the expander 10 to be deployed in the incorrect position.

When the distal end region 44 of the delivery tube 42 has been advanced sufficiently along the urethra, for example to the bladder neck 32 or prostatic urethra 30 the clinician may move the lever 49 to the partially deployed position. This unlocks the proximal and distal grips 41, 43 such that the clinician may pull the proximal grip 41 back relative to the distal grip 43 to move the grips 41, 43 and the delivery tube 42 to the partially-deployed position.

Figure 11:
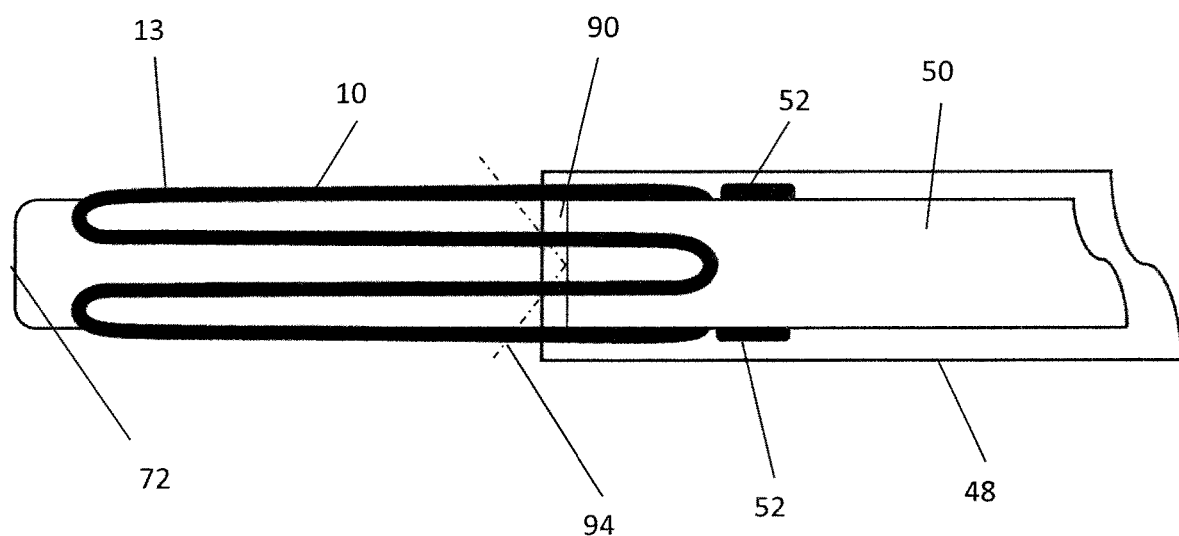
FIG. 11 is a schematic side view of the distal end region of the delivery tube and expander in a partially deployed configuration.

FIG. 11 shows a schematic plan view of the distal end region 44 of the delivery tube 42 in the partially deployed position in which the outer sleeve 48 has been retracted to partially unsheathe the expander 10. When in the partially deployed position the end of the outer sleeve 48 is positioned distally of the retention formations 52 but proximally of the distal end 13 of the expander 10. As such, the expander 10 is partially unsheathed but is still retained on the inner tube 50. From this position the clinician may operate the handle 46 to return the outer sleeve 48 to the stored position if they do not want to proceed with deploying the expander 10. Moving the outer sleeve 48 to the partially deployed position causes the telescope 90 to move proximally, to the partially deployed position, such that the distal end 13 of the expander 10 is within the field of view 94 of the telescope 90.

Figure 12:
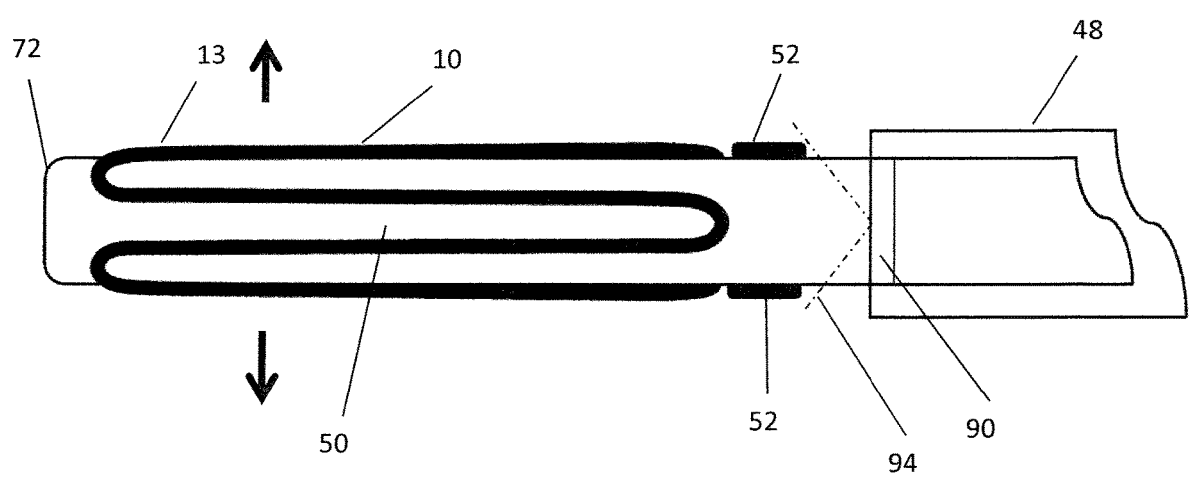
FIG. 12 is a schematic side view of the distal end region of the delivery tube and expander in a fully deployed configuration.

Once the clinician is satisfied that the expander 10 is located correctly within the prostatic urethra 30 they may move the lever 49 from the partially deployed position to the fully deployed position such that the distal grip 43 may be moved longitudinally towards the proximal grip 41 to the fully deployed position. This moves the outer sleeve 48 and telescope 90 proximally relative to the inner tube 50 as shown in FIG. 12 in which the expander 10 and retention formations 52 are fully uncovered by the outer sleeve 48. Uncovering the retention formations 52 allows the expander 10 to disengage the retention formations 52 and expand radially to the deployed position.

The three stages of deployment, namely: stowed, partially deployed and fully deployed beneficially allow the clinician to deploy the expander 10 in a controlled manner and mitigates the potential for the expander 10 to be accidentally deployed or deployed in the wrong location. The lever 49 prevents accidental operation of the handle 46 that may cause the expander 10 to be deployed incorrectly. Furthermore, the inner tube 50 may be held static relative to the anatomy during operation of the handle 46 as the telescope 90 moves inside it, allowing the anatomy to be visualised with the expander 10. This improves the accuracy of deployment of the expander 10 and promotes radial expansion of the expander 10 during deployment with minimal longitudinal movement relative to the anatomy.

Figure 13:
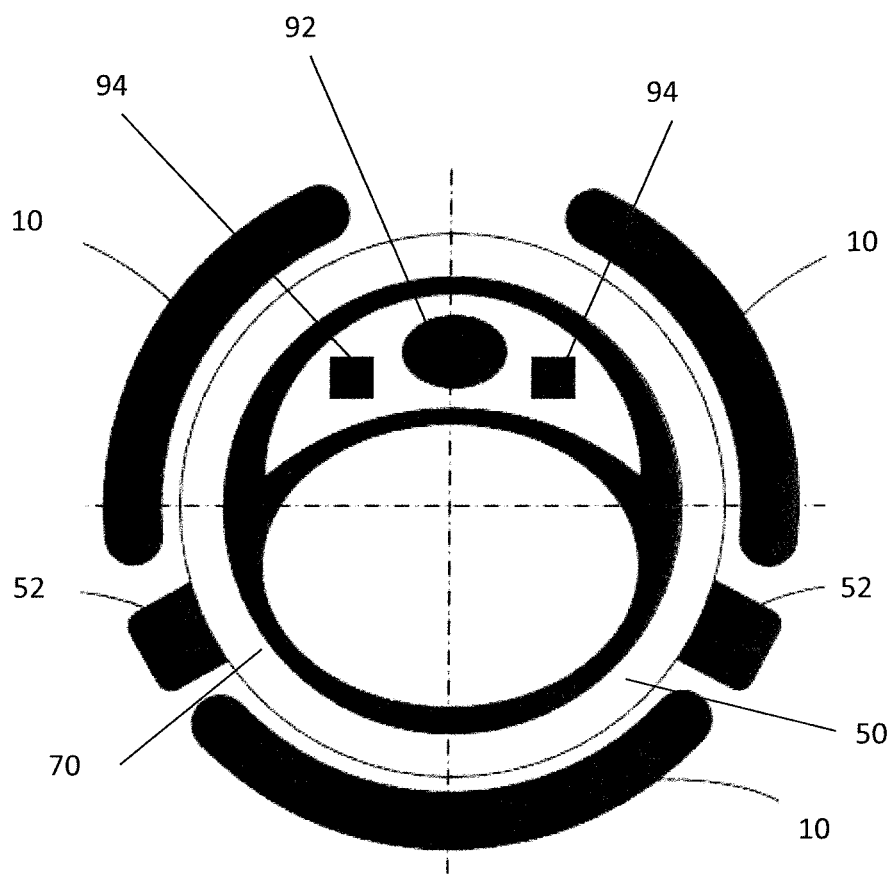
FIG. 13 is a schematic end view of the delivery device comprising an imaging device.

FIG. 13 shows an end on view of the inner tube 50 and expander 10 in a stored configuration with the outer sleeve 48 removed for clarity. The inner tube 50 comprises an imaging device 90 such as a telescope or imaging chip located within the inner lumen 70. The imaging device 90 shown comprises an electronic imaging chip 92, such as a CMOS chip and at least one light source 94 for illuminating the region that is being imaged by the imaging device 90. The light source 94 may be, for example, an LED or optical fibre configured to illuminate the area that is to be imaged by the imaging device 90.

The imaging chip 92 has a wide field of view, for example 120° or more such that the clinician may view a large area of the anatomy. As shown in FIGS. 10 to 12 the field of view 94 of the imaging device 90 extends through the expander 10 when the expander 10 is retained on the distal end 44 of the inner tube 50 when the outer sleeve 48 is in the stored configuration. This is advantageous as it allows the clinician to view the expander 10 relative to the anatomy which assists the clinician when positioning the expander 10 angularly and longitudinally within the prostatic urethra 30.

As shown in FIG. 10, when the outer sleeve 48 is in the stored position the field of view 94 of the imaging device 90 extends through the outer sleeve 48. However, in FIG. 11 when in the partially deployed position the outer sleeve 48 is retracted such that it is no longer in the field of view 94 of the imaging device 90. As such, the partially deployed position is beneficial as the outer sleeve 48 is retracted out of the field of view of the imaging device 90 thereby improving the clarity of the image provided to the clinician. Furthermore, the partially deployed position allows the distal prongs 14 of the expander 10 to contact the lobes of the prostate 11 within the prostatic urethra 30 such that the clinician may view the expander 10 contacting the prostatic urethra 30 prior to full-deployment. This advantageously enables a clinician to check if the expander 10 is positioned correctly prior to full deployment.

Figure 14:
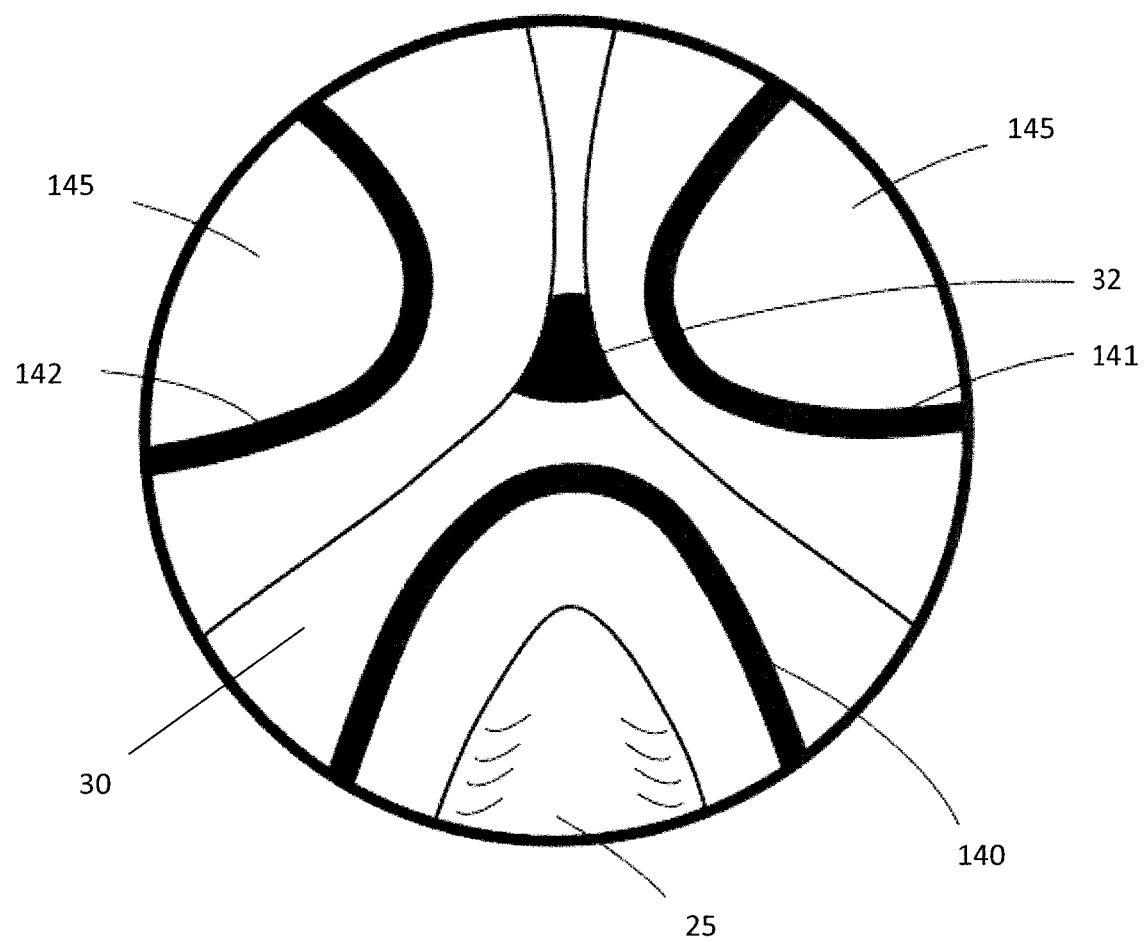
FIG. 14 is a schematic view of an image captured by the imaging device of FIG. 13.

FIG. 14 is a schematic of an image captured by the imaging device 90 when the outer sleeve 48 is in the partially deployed position. The image shows each of the distal prongs 14 of the expander 10 aligned with and contacting the lateral prostatic lobes. Furthermore, the posterior prong 140 of the expander is shown surrounding the verumontanum 25. The two anterior prongs 141, 142 of the expander 10 are orientated such that they engage the anterior lobes of the prostatic urethra 30. The image provided to the clinician by the imaging device 90 beneficially allows to visualise the longitudinal position of the expander 10 relative to the anatomy, for example the verumontanum 25 and the bladder neck 32 and also the angular position of the expander 10 relative to the prostatic lobes. This improves the accuracy of positioning the expander 10 within the prostatic urethra 30.

Figure 15:
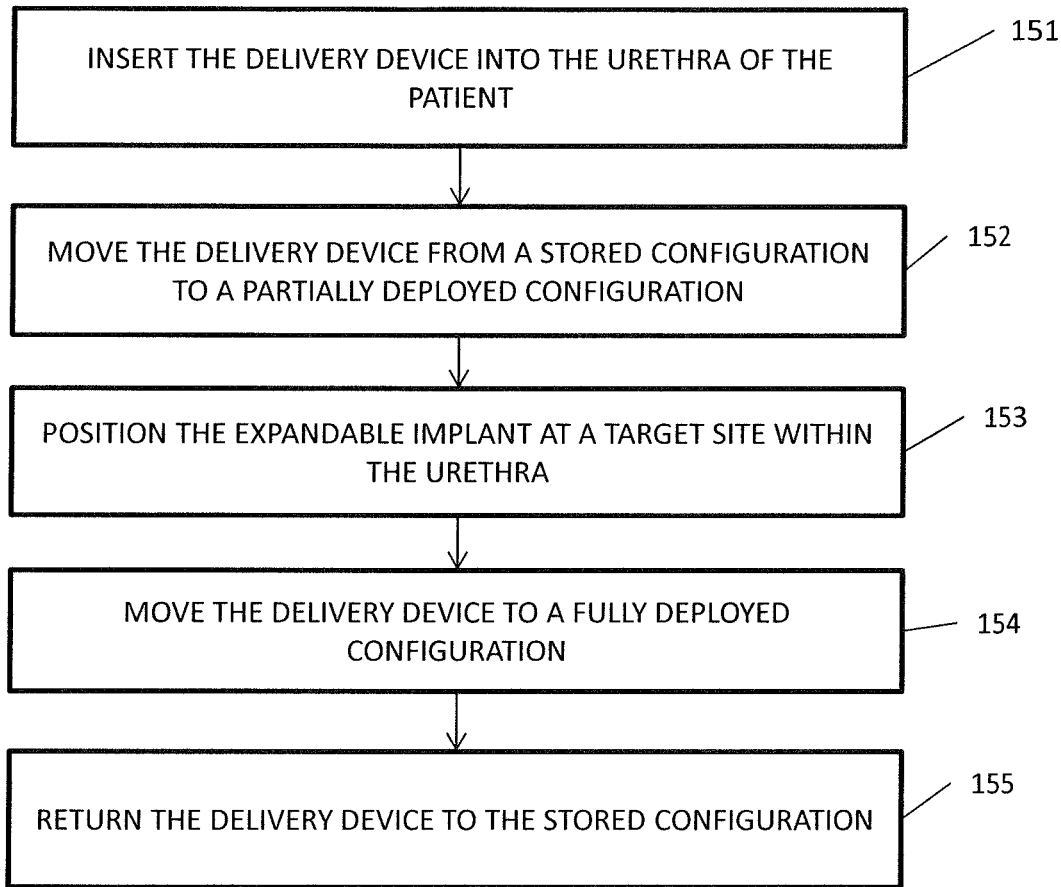
FIG. 15 is a flow chart outlining the steps of deploying an expandable implant using the delivery device of FIG. 4.

Turning now to FIG. 15 a flow chart outlining a method of deploying the expandable implant within the prostatic urethra 30 is shown. In the first step 151 the clinician inserts the delivery device 40 into the urethra of the patient via the penis. In particular, the clinician inserts the delivery tube 42 into the urethra of the patient. The delivery tube 42 is inserted into the urethra in the stored configuration such that the expander 10 is covered by the outer sleeve 48.

The delivery tube 42 is advanced along the urethra until the distal end of the delivery tube 42 reaches the bladder neck 32. As the delivery tube 42 is advanced along the urethra the clinician may view the anatomical landmarks, for example the external sphincter 33, the verumontanum 25 and the bladder neck 32, of the patient from the image captured by the imaging device 90. This is beneficial as it allows the clinician to assess the patient and to check for any structures that may prevent the expander 10 being deployed, for example for an obstructing intravesical median lobe.

Next, in Step 152, the clinician moves the delivery device 40 from the stored configuration to the partially deployed position. The clinician moves the lever 49 from the stored position to the partially deployed position and then moves the distal grip 43 in a proximal direction to move the outer sleeve 48 in a proximal direction relative to the expander 10 and the inner tube 50 such that the expander 10 is partially uncovered. This is beneficial as moving the outer sleeve 48 and telescope to the partially deployed position allows the clinician to view the distal prongs of the expander 10 relative to the lateral prostatic lobes.

In Step 153 the clinician positions the expander 10 at a target site, for example the prostatic urethra 30, by moving the distal end region 44 of the delivery tube 42 in a proximal direction from the bladder neck 32 with the aid of graduation marks on the outside of the delivery tube 42 to approximate the axial distance travelled from the bladder neck 32. The bladder neck 32 may be used as a datum for positioning the expander 10 longitudinally within the prostatic urethra 30.

When the clinician is satisfied that the distal end region 44 and thus the expander 10 are positioned in the correct longitudinal position the clinician may then rotate the delivery device 40 to orientate the expander 10 within the target site. The expander 10 is orientated such that the distal apices 15 of the expander 10 that are visible on the image captured by the imaging device 90 are aligned with the prostatic lobes within the prostatic urethra 30. The clinician may move the delivery tube 42 in a further distal direction when the expander 10 is in the correct orientation such that the verumontanum 25 comes into view 10 can be placed in a clinically acceptable position in between the bladder neck 32 and verumontanum, 25 with the apices circumferentially targeting the lateral lobes.

If the clinician is satisfied that the expander 10 is correctly positioned within the prostatic urethra 30 then they may move the delivery device 40 to the fully deployed position in Step 154. Alternatively, if the clinician is unsatisfied with the position of the expander 10 the delivery device 40 may be returned to the stored configuration and the procedure may be aborted.

The delivery device 40 is moved to the fully deployed configuration by first moving the lever 49 to the fully deployed position before moving the distal grip 43 in a proximal direction. This moves the outer sleeve 48 and telescope in a proximal direction whilst maintaining the inner tube 50 and thus expander 10 in a static position relative to the target site. In a further embodiment, the inner tube 50 may be a camera lumen that moves in the proximal direction whilst the expander 10 is maintained in a static position relative to the target site. This is beneficial as it ensures the expander 10 is deployed in the intended position. When the outer sleeve 48 is moved to the fully deployed position the proximal apices 18 disengage the retention features 52 and expand in an outward radial direction. The walls 80, 82 of the slot 58 promote radial expansion of the expander 10 and minimise longitudinal movement of the expander 10 during deployment.

After the expander 10 has been deployed the delivery device 40 may be returned to the stored or partially deployed configuration in Step 155. Returning the delivery device 40 to the stored or partially deployed configuration is beneficial as the outer sleeve 48 covers the retention formations 52. This is beneficial as it reduces the chance of the retention formations 52 inadvertently re-engaging the expander 10 after deployment which may cause the expander 10 to move. The clinician may view the deployed expander 10 through the imaging device 90 to check that the expander 10 is correctly positioned. When the clinician is satisfied that the expander 10 has been deployed correctly the delivery device 40 may be moved in a proximal direction to withdraw the device from the urethra.

Figure 16:
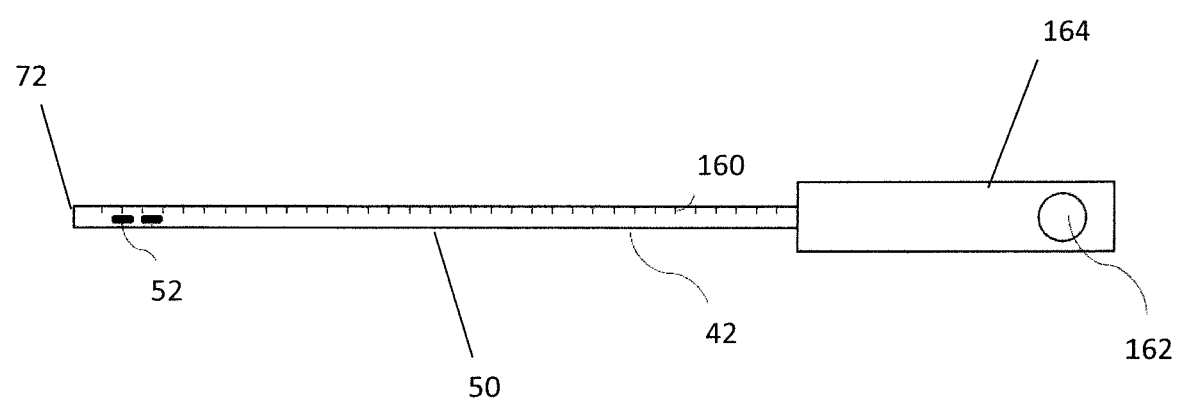
FIG. 16 is a schematic view of a delivery device according to another embodiment.

Turning now to FIG. 16, an embodiment of the delivery device 40 is shown in which the delivery tube 42 comprises a series of graduation marks 160 spaced at known intervals along the length of the delivery tube 42 to allow positioning of the expander 10, that is in a fixed position to the delivery tube 42 with the bladder neck 32. FIG. 16 shows a schematic of the inner tube 42 comprising an overmoulded hub 164 attached to a proximal end of the inner tube 50. The hub 164 comprises a boss hole 162 for attaching the hub 164 to the handle 46. The boss hole feature 162 ensures the relative position of the inner tube 42 to the proximal grip 41 is maintained.

The graduation marks 160 are shown on the inner tube 50. However, the graduation marks 160 may be on the inner tube 50 or on the outer sleeve 48. The graduation marks 160 are visible to the clinician as the delivery tube 42 is advanced along the urethra thereby giving the clinician an indication of the longitudinal position of the distal tip 72 of the inner tube 50 within the urethra. The skilled reader will understand that the graduation marks 160 may be positioned at any known interval suitable for positioning the delivery tube 42 longitudinally within the urethra. Furthermore the graduation marks 160 may be numbered. The graduation marks can also be used to approximate the prostatic urethral length during the procedure, which may guide the clinician to select the most clinically acceptable position for the expander 10.

The graduation marks 160 may be used when the distal tip 72 of the inner tube 50 is located at the bladder neck 32 prior to moving the delivery tube 42 in a proximal direction. This is beneficial as the clinician may know that, for example, the expander 10 should be located two graduation marks proximally from the bladder neck 32. In this instance, when the proximal tip of the delivery tube 42 is located at the bladder neck 32 the clinician may then retract the delivery tube 42 by two graduation marks 160 to position the expander 10 in the approximate longitudinal position. The clinician can read the graduation marks along the portion of the delivery tube 42 within the patient or outside the patient.

A delivery device 40 according to a further embodiment is described below with reference to FIGS. 17 to 26. For clarity, reference numerals for comparable features have been kept consistent across the two embodiments.

Figure 17:
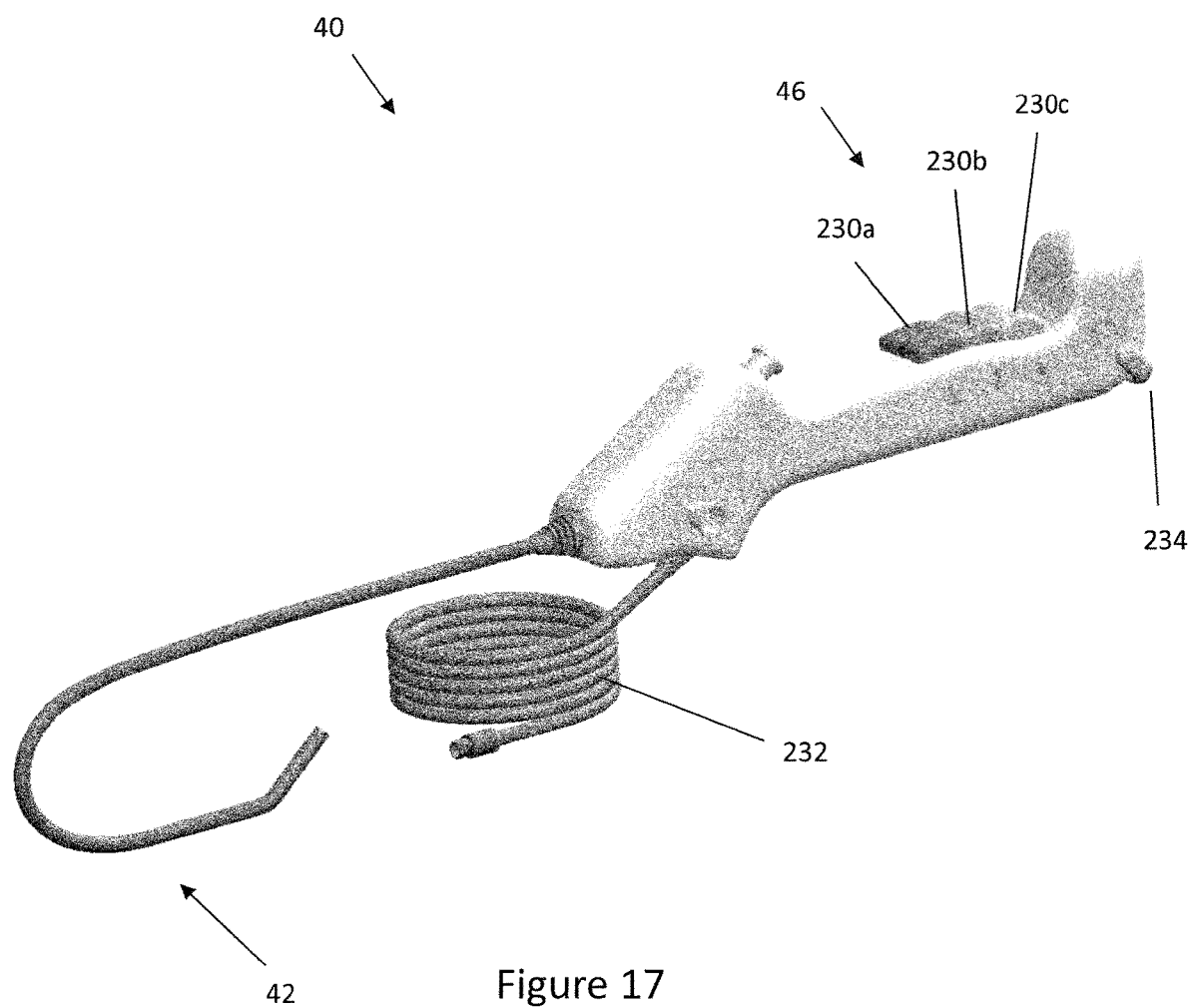
FIG. 17 is a perspective view of a delivery device according to a further embodiment of the invention.

FIG. 17 shows a perspective view of the delivery device 40 according to the further embodiment. The delivery device 40 comprises a handle 46 operatively connected to a flexible delivery tube 42. The delivery tube 42 is configured to at least partially receive the expander 10 in a compressed state and to position and deploy the expander 10 within the prostatic urethra 30 of the patient. The delivery tube 42 is similar to the previous embodiment in that it comprises an inner tube 50 surrounded by an outer sleeve 48 moveable between a stored position, a partially deployed position and a fully deployed position. However, the delivery device shown in FIG. 17 further comprises an intermediate or steering tube (not shown in FIG. 17) surrounding the inner tube 50 and being surrounded by the outer sleeve 48. The steering tube is described in further detail below.

The delivery tube 42 of the delivery device 40 shown in FIG. 17 is flexible which is beneficial as it can bend and flex to conform to the path of the urethra of the patient thereby reducing the discomfort experienced by the patient. The steering tube allows the position of the distal tip region 44 to be controlled which beneficially assists in the insertion and positioning of the delivery tube 42 within the patient. Furthermore, the steerable delivery tube 42 allows the imaging device 90 of the delivery tube 42 to be moved to provide a wider field of view to the clinician.

Figure 18:
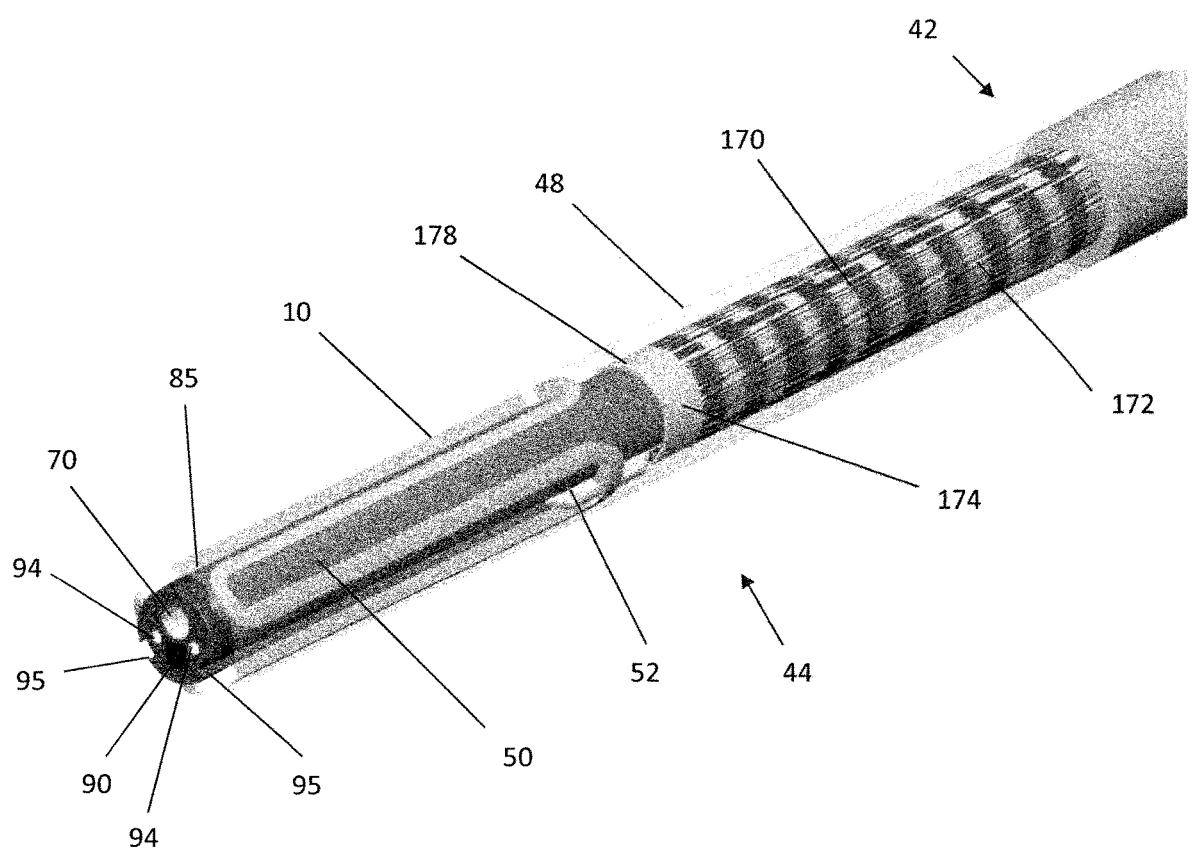
FIG. 18 is a perspective view of the distal tip of the delivery device of FIG. 17.

FIG. 18 shows a perspective view of the distal tip region 44 of the delivery tube 42. The distal end region 44 of the outer sleeve 48 has been shown as transparent in FIG. 18 for clarity. As shown in FIG. 18 the steering tube 170 surrounds the inner tube 50 and is surrounded by the outer sleeve 48. The steering tube 170 is an elongate flexible plastics tube with a braided distal end 172. The steering tube 170 is operable via the handle 46 to vary the position of the distal tip region 44 and thus the expander 10 by a clinician. Furthermore, the retention features 52 are secured to and extend distally from the braided distal end 172. The retention features 52 are configured to engage the expander 10 and prevent longitudinal or circumferential movement of the expander 10 relative to the steering tube 170.

Figure 19:
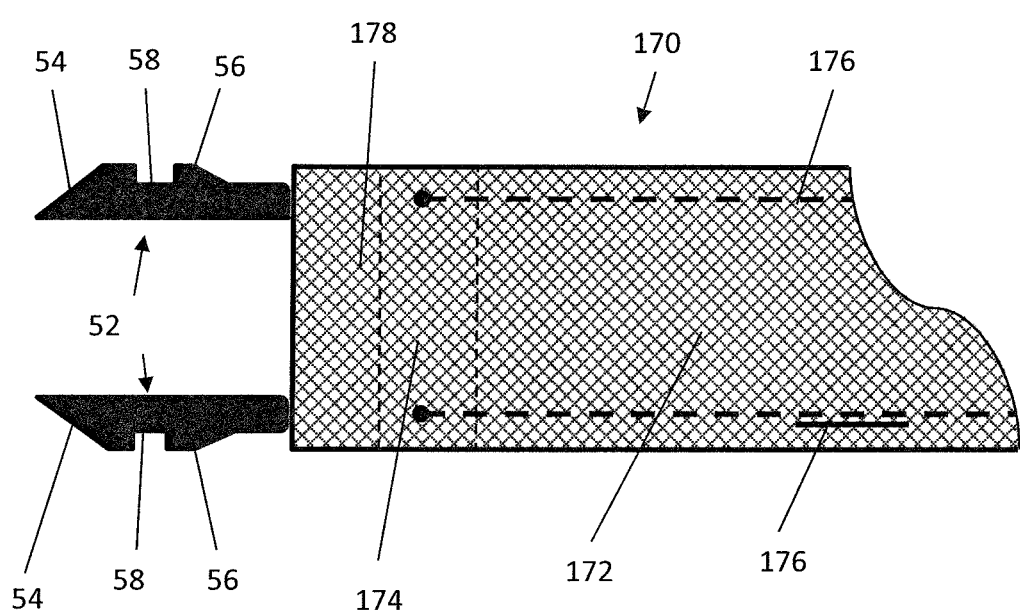
FIG. 19 is a schematic side view of the distal end region of a steering tube of the delivery device of FIG. 17.

The distal end of the steering tube 170 is shown schematically in FIG. 19 with the inner tube 50 and outer sleeve 48 removed for clarity. The steering tube 170 comprises a steering ring 174 at the distal end 178 of the braided portion 172. Two steering wires 176 are connected to opposing sides of the steering ring 174 and extend proximally along the length of the steering tube 170 to the handle 46. The steering wires 176 are operably coupled to the handle 46 such that a clinician may operate the handle 46 to vary the tension in the steering wires 176. This causes the position of the steering ring 174, and thus the expander 10, to be controlled by a clinician operating the handle 46.

The steering tube 170 further comprises two retention formations 52 for retaining the expander 10 on the delivery tube 42. The retention formations 52 are elongate tabs that extend distally from the distal end 178 of the braided portion 172 such that the retention formations protrude from the end of the intermediate tube 170. The retention formations 52 comprise a retention slot 58 for retaining the expander 10 and are spaced angularly on the steering tube 170 such that the expander 10 is orientated to align with the prostatic lobes when the delivery tube 42 is inserted within the patient.

As shown in FIG. 19, the retention formations 52 comprise proximal protrusion 56 and a distal protrusion 54 with a retention slot 58 defined therebetween. The retention slot 58 is configured to at least partially receive a proximal end 16 of the expander 10 thereby inhibiting longitudinal or circumferential movement of the expander 10 relative to the inner tube 50. When the outer sleeve 48 surrounds the retention formations 52, for example in the stored or partially deployed configuration the outer sleeve 48 surrounds the retention formations 52 and prevents the expander 10 from expanding radially and disengaging the retention formations 52.

The inner tube 50 is moveable in a longitudinal direction relative to the steering tube 170 between a distal position (as shown in FIG. 18) and a retracted position. When in the retracted position the distal tip 72 of the inner tube 50 is located between the proximal end 16 and the distal end 13 of the expander 10. Moving the inner tube 50 between a distal position and a retracted position is beneficial as it varies the position of the imaging chip 92 relative to the expander 10. When the inner tube 50 is in the distal position the imaging chip 92 is positioned distally of the distal end 13 of the expander 10 such that expander is not within the field of view of the imaging chip 92. Conversely, when the inner tube 50 is in the retracted position the distal end of the expander 10 is within the field of view of the imaging chip 92. This is beneficial as it allows the distal end 13 of the expander 10 to be imaged relative to the anatomy within the prostatic urethra 30 of the patient.

As shown in FIG. 18 the inner tube 50 comprises two grooves 95 extending in a longitudinally in a proximal direction from the distal tip 72 of the inner tube 50. The grooves 95 are configured to at least partially receive the retention formations 52. This is advantageous as it reduces the overall diameter of the delivery tube 42 as the grooves 95 allow a portion of the retention formations 52 to be received within the grooves 95. Furthermore, the grooves 95 allow the inner tube 50 to be moved between the distal position and the retracted position relative to the steering tube 170.

Figure 20:
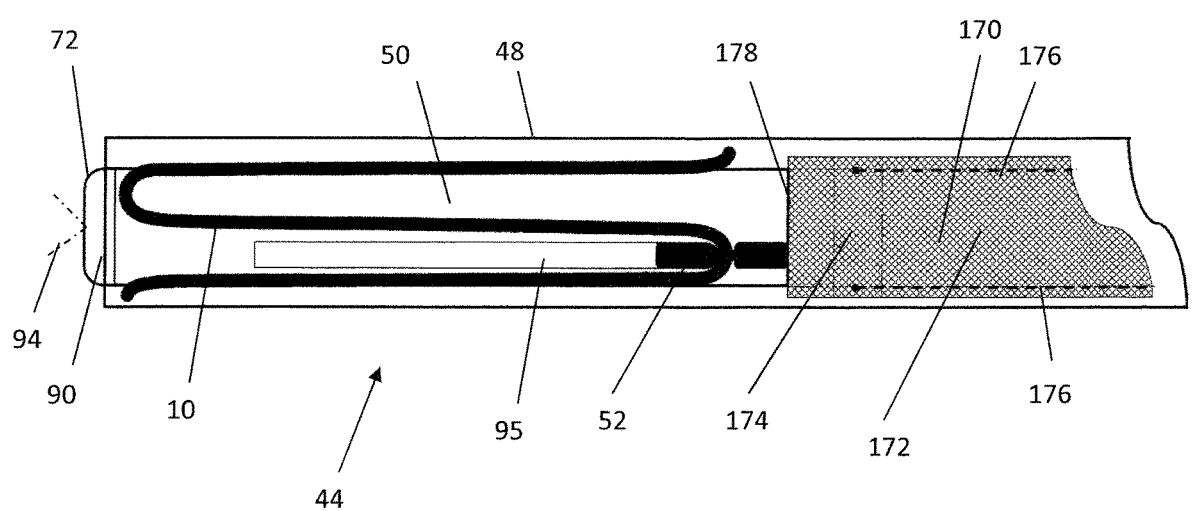
FIG. 20 is a schematic view of the distal end region of the delivery device of FIG. 17 in the stored configuration.

FIG. 20 shows a schematic view of one embodiment of the distal end region 44 of the delivery tube 42 in the stored configuration. When in the stored configuration the inner tube 50 is in the distal position and the outer sleeve 48 is in the stored position such that the outer sleeve 48 surrounds the expander 10. The distal tip 72 of the inner tube 50 extends distally of the distal end of the outer sleeve 48 when the inner tube 50 is in the distal position. This beneficially allows the imaging chip 92 to capture images of the anatomy that are not obscured by the expander 10 or the outer sleeve 48. Furthermore, the inner tube 50 supports the expander 10 over its longitudinal length when the inner tube 50 is in the distal position. This is beneficial when the delivery tube 42 is being inserted into, and along, the urethra as the inner tube 50 prevents the expander 10 deflecting inwardly which may cause the expander 10 to disengage the retention formations 52.

Figure 21:
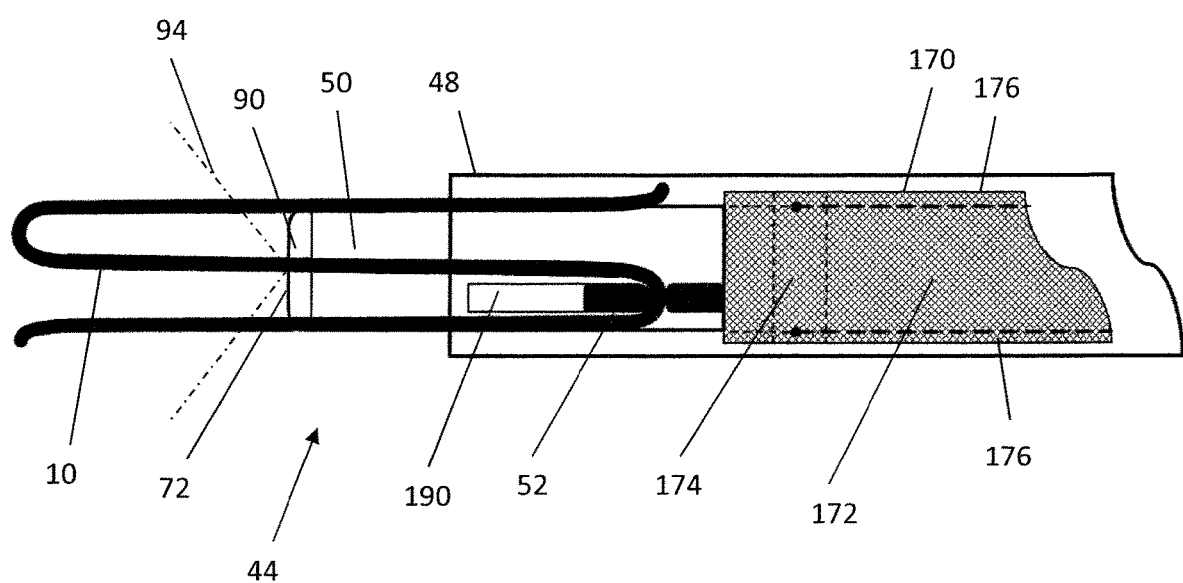
FIG. 21 is a schematic view of the distal tip of the delivery device of FIG. 17 in the partially-deployed configuration.

Turning now to FIG. 21, the delivery tube 42 is shown in the partially deployed configuration. In the partially deployed configuration both the inner tube 50 and the outer sleeve 48 have been moved proximally relative to the expander 10 such that the distal end 13 of the expander is unsheathed. Furthermore, the inner tube 50 is in the retracted position such that the distal tip 72 of the inner tube 50 is located between the proximal and distal ends of the expander 10. As shown in FIG. 21, when the delivery device 42 is in the partially deployed position the distal end of the outer sleeve 48 is located proximally of the distal tip 72 of the inner tube 50 and distally of the retention formations 52. This is beneficial as the outer sleeve 48 retains the expander 10 in the stored configuration whilst not obscuring the field of view of the imaging chip 92.

Figure 22:
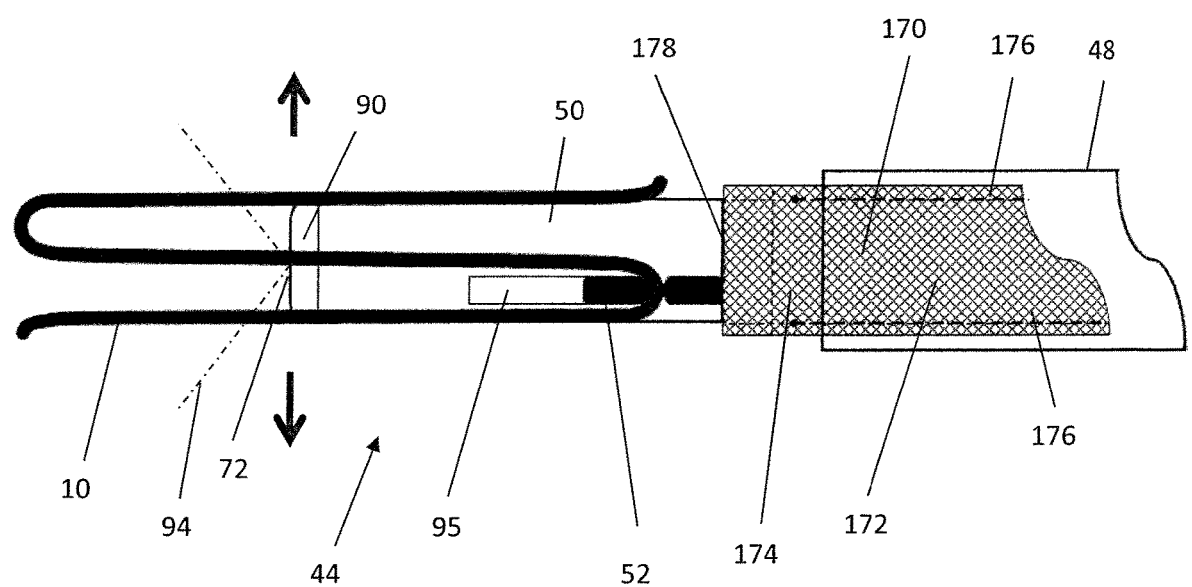
FIG. 22 is a schematic view of the distal tip of the delivery device of FIG. 17 in the fully-deployed configuration.

FIG. 22 shows a schematic view of the distal end region 44 of the delivery tube 42 in the fully-deployed configuration. In the fully-deployed position the outer sleeve 48 is moved proximally such that the distal end of the outer sleeve 48 is located proximally of the retention features 52. This fully uncovers the expander 10 and allows the expander 10 to expand radially and disengage the retention formations 52.

Figure 23:
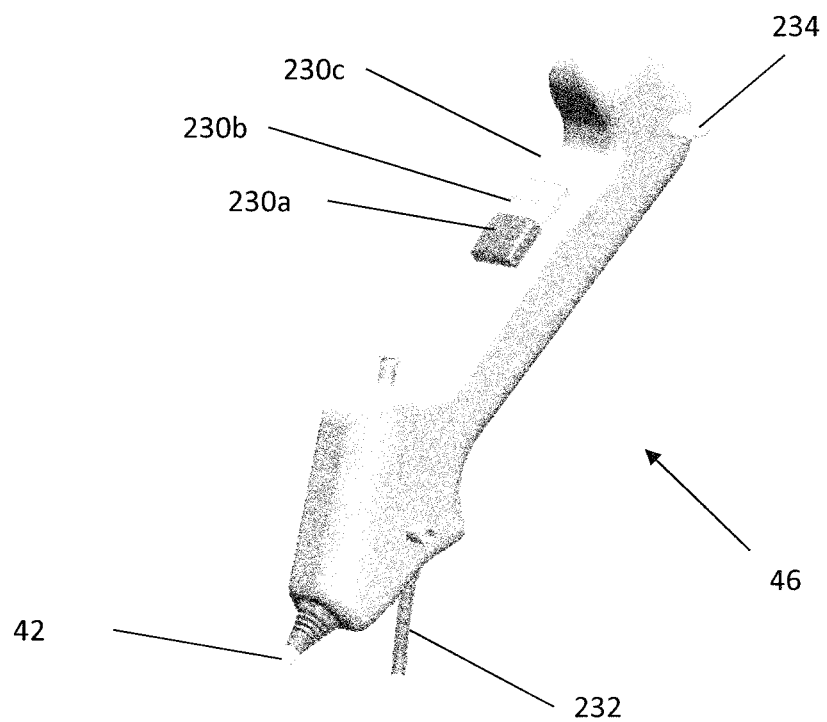
FIG. 23 is a perspective view of the handle of the delivery device of FIG. 17.

Turning now to FIG. 23, a perspective view of the handle 46 is shown. The handle 46 comprises three buttons 230a, 230b, 230c that are operable by the clinician to move the delivery tube 42 between the stored, partially-deployed and fully-deployed configurations as outlined in FIGS. 20 to 22. The buttons 230a, 230b, 230c allow the clinician to easily move the delivery tube 42 between the various configurations. The handle 46 further comprises a lever 234 that is connected to the steering wires 176. The lever 234 may be operated to vary the tension in the wires and thus control the position of the steering tube 170.

The handle 46 may further comprise a lever or button that can lock the delivery tube 42 in a configuration. This may be beneficial as it would prevent the clinician inadvertently moving the delivery tube 42 to the partially-deployed or fully deployed position before the delivery tube 42 is positioned correctly within the patient.

Figure 24:
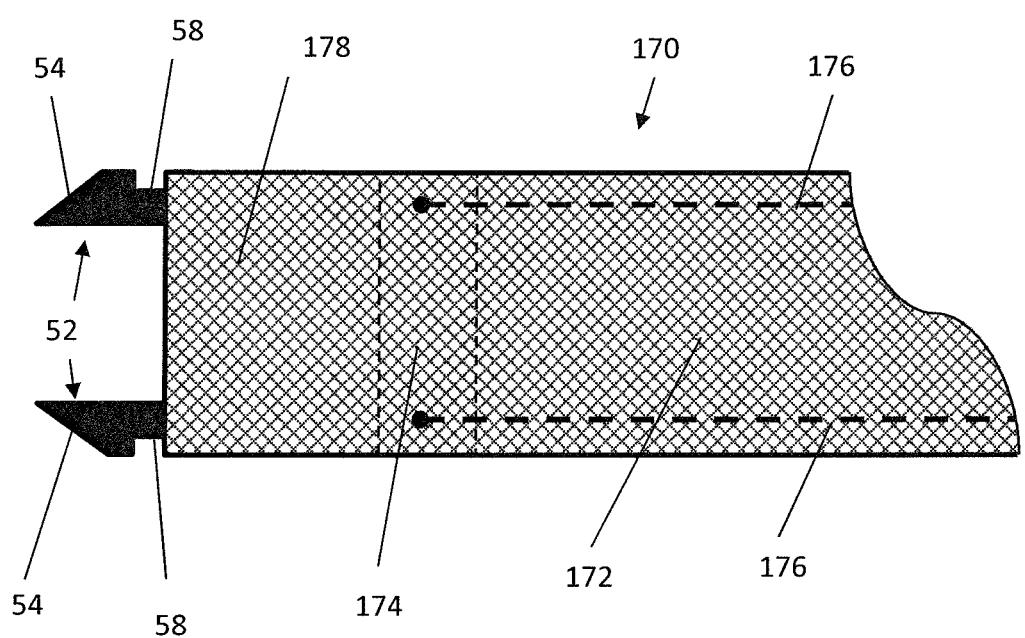
FIG. 24 is a schematic side view of the distal end region of a steering tube according to another embodiment.

FIG. 24 shows an alternative embodiment of the steering tube 170. In FIG. 24 the retention features 52 extend from the distal end 178 of the steering tube 170. The retention formation 52 each comprise distal protrusion 54. A retention slot 58 is defined between the distal end 178 of the steering tube 170 and the distal protrusion 54. The expander 10 may be partially received within the retention slot 58 defined between the distal protrusion 54 and the distal end 178 of the braided portion 172 of the steering tube 170. The retention formation 52 may be connected to, and extending distally from, the steering ring 174.

Figure 25:
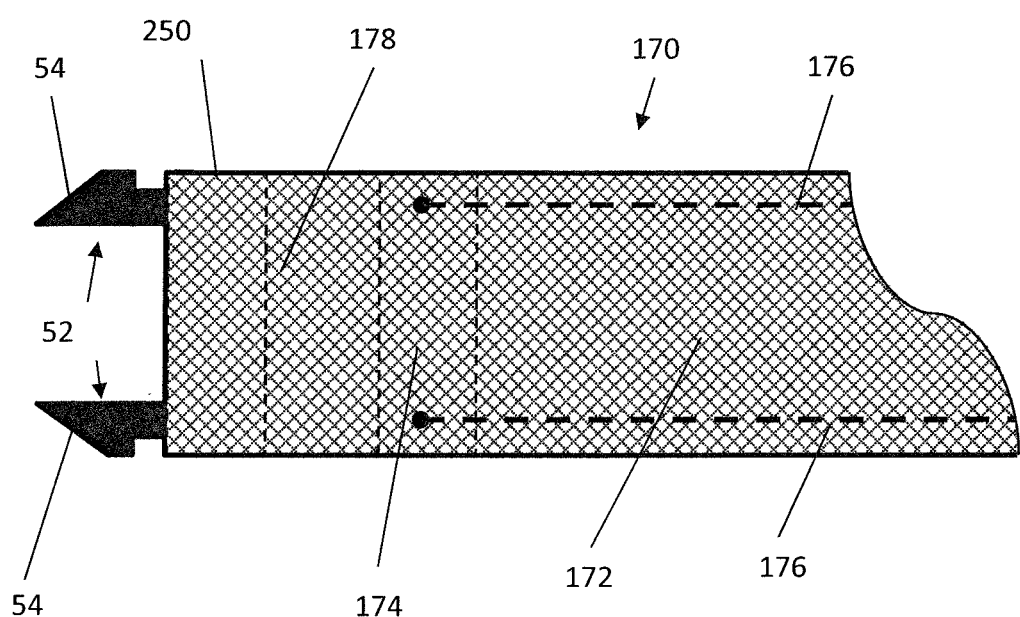
FIG. 25 is a schematic side view of the distal end region of a steering tube according to another embodiment.

FIG. 25 shows a further embodiment of the steering tube 170. In FIG. 25 the retention features 52 extend from the distal end of the steering tube 170 as described above in relation to FIG. 24. However, in FIG. 25 the retention formation 52 is attached to and extending from a retaining ring 250. The retention formations 52 and retaining ring 250 may form a discrete sub-assembly that can be coupled to the steering tube 170.

Figure 26:
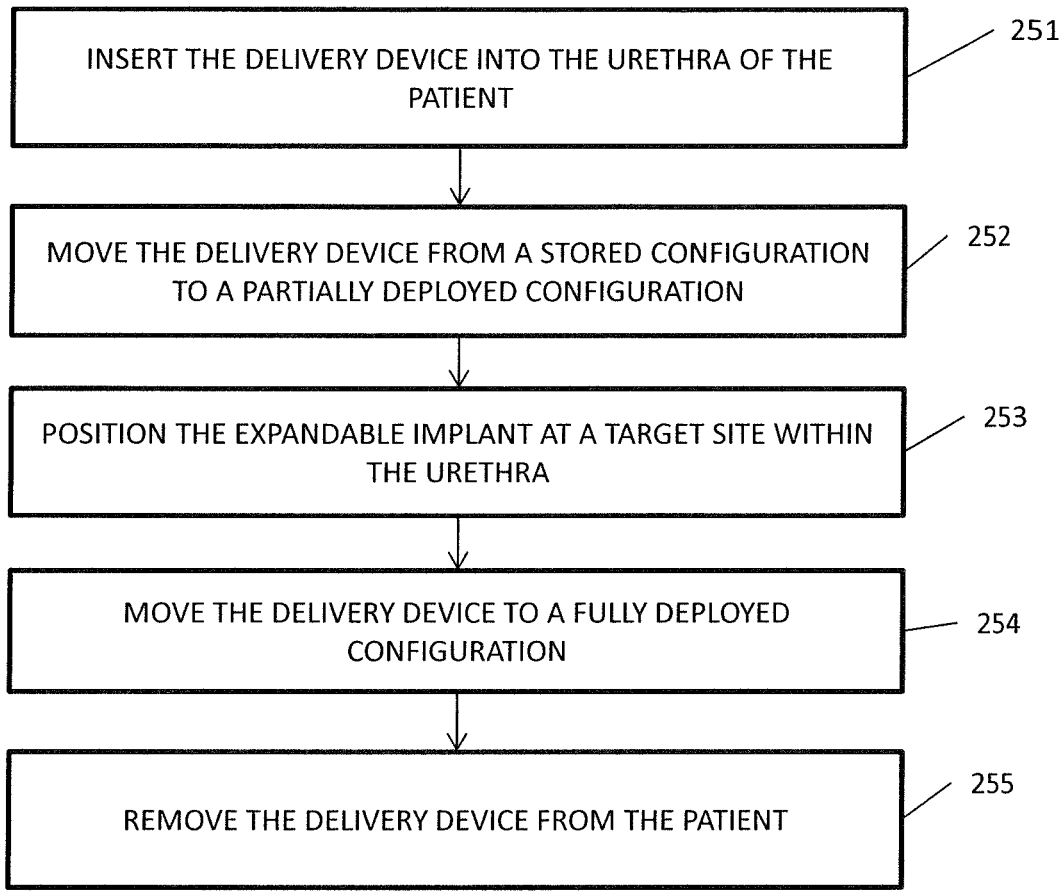
FIG. 26 is a flow chart outlining the steps of deploying an expandable implant using the delivery device of FIG. 17.

Turning now to FIG. 26, a flow chart outlining a method of deploying the expandable implant 10 within the prostatic urethra 30 is shown. In the first step 251 the delivery device 40 is inserted into the urethra of the patient via the penis. The deliver device 40 is inserted in the stored configuration where the outer sleeve 48 surrounds the expander 10 thereby retaining the expander 10 in the stored configuration. The clinician may operate the handle 46 to control the steering ring 174 and vary the angle of the distal tip region 44 of the delivery tube 42 to aid insertion of the delivery tube 42 along the urethra.

The distal end of the delivery tube 42 is advanced along the urethra until the distal end of the delivery tube 42 reaches the bladder neck 32. In Step 252 the delivery device is moved from the stored configuration to a partially deployed position. In the partially deployed position the inner tube 50 is retracted such that the imaging chip 92 may view the distal end 13 of the expander 10. Furthermore, the outer sleeve 48 is also retracted such that the distal end 13 of the expander 10 is unsheathed but the proximal end 16 remains sheathed and retained on the retention formations 52.

In Step 253 the clinician positions the expander 10 at a target site, for example the prostatic urethra 30, by moving the distal end region 44 of the delivery tube 42 in a proximal direction from the bladder neck 32 with the aid of graduation marks on the outside of the delivery tube 42 to approximate the axial distance travelled from the bladder neck. The bladder neck 32 may be used as a datum for positioning the expander 10 longitudinally within the prostatic urethra 30. When the clinician is satisfied that the distal end region 44 and thus the expander 10 are positioned in the correct longitudinal position the clinician may then rotate the delivery device 40 to orientate the expander 10 within the target site. The expander 10 is orientated such that the distal apices 15 of the expander 10 that are visible on the image captured by the imaging device 90 are aligned with the prostatic lobes within the prostatic urethra 30. The clinician may move the delivery tube 42 in a further distal direction when the expander 10 is in the correct orientation such that the verumontanum 25 comes into view and so that the expander 10 can be placed in a clinically acceptable position in between the bladder neck 32 and verumontanum 25, with the apices circumferentially targeting the lateral lobes.

In Step 254, when the clinician is satisfied with the position of the expander 10 the outer sleeve 48 is moved to the fully deployed position such that the expander 10 is deployed within the prostatic urethra 30 of the patient. Finally, in Step 255 the delivery tube 42 is removed from the urethra of the patient. The delivery tube 42 may be removed from the patient in the fully deployed position or the clinician may move the delivery tube 42 to the partially deployed or stowed positions.

The clinician may use the imaging chip 92 to view the expander 10 in the deployed position to confirm that the expander 10 has been deployed correctly within the prostatic urethra 30.

It will be appreciated that various changes and modifications can be made to the present invention without departing from the scope of the present application.

The invention claimed is:

1. A method of treating benign prostatic hyperplasia, the method comprising;
   inserting a distal end of an outer sleeve of an implant delivery device through a urethra,
      the outer sleeve comprising a hollow distal segment holding an implant in a contracted state,
      the implant being self-expandable from the contracted state to an expanded state,
      the implant comprising a single filament bent to comprise a plurality of proximal apices, a plurality of distal apices, and a plurality of struts extending between the proximal apices and the distal apices,
      the delivery device comprising a handle comprising an actuator,
      the outer sleeve extending distally from the handle,
      the delivery device comprising an inner tube comprising a plurality of proximal protrusions and a plurality of distal protrusions, each of the plurality of proximal protrusions paired with one of the plurality of distal protrusions to form a plurality of slots each containing one of the plurality of proximal apices of the implant, the plurality of proximal protrusions configured to inhibit proximal movement of the implant in the delivery device and the plurality of distal protrusions configured to inhibit distal movement of the implant in the delivery device and to inhibit rotational movement of the implant relative to the inner tube,
      the actuator being operable to retract the outer sleeve,
      the delivery device comprising a light emitter, and
      the delivery device comprising an imaging device;
   operating the actuator to partially retract the outer sleeve so that the implant is partially uncovered, and so that the proximal apices contained in the plurality of slots prior to the outer sleeve being partially retracted remain contained in the plurality of slots after the outer sleeve is partially retracted;
   illuminating the urethra with the light emitter;
   rotationally orienting the partially uncovered implant with respect to anatomical features of the urethra while using the imaging device; and
   operating the actuator to further retract the outer sleeve to deliver the implant in the urethra aligned with prostatic lobes of the urethra and so a verumontanum and seminal ducts are unobstructed.

2. The method of claim 1, wherein the anatomical features comprise at least one of a prostatic lobe, a bladder neck, or the verumontanum.

3. The method of claim 1, wherein operating the actuator to partially retract the outer sleeve comprises moving a safety catch to a first position, and wherein operating the actuator to further retract the outer sleeve comprises moving the safety catch to a second position different than the first position.

4. The method of claim 1, wherein inserting the distal end of the outer sleeve of the implant delivery device through the urethra comprises steering the delivery device.

5. The method of claim 1, wherein after delivering the implant in the urethra the implant is between a bladder neck and an external sphincter.

6. The method of claim 1, wherein operating the actuator to partially retract the outer sleeve comprises proximally retracting the imaging device to provide a view of the plurality of distal apices relative to the anatomical features of the urethra to aid orientation and placement of the implant.

7. A method of treating benign prostatic hyperplasia, the method comprising:

inserting a distal end of an outer sleeve of an implant delivery device through a urethra,
 the outer sleeve comprising a hollow distal segment holding an implant in a contracted state,
 the implant being expandable from the contracted state to an expanded state,
 the implant comprising a plurality of proximal apices, a plurality of distal apices, and a plurality of struts extending between the proximal apices and the distal apices,
 the delivery device comprising a handle comprising an actuator,
 the outer sleeve extending distally from the handle,
 the delivery device comprising an inner tube comprising a space engaging one of the plurality of proximal apices of the implant, and
 the delivery device comprising an imaging device;
operating the actuator to change a relative longitudinal position between the inner tube and the outer sleeve so that the implant is partially uncovered and so that the one of the plurality proximal apices engaged with the space prior to the implant being partially uncovered remains engaged with space after the implant is partially uncovered;
rotationally orienting the partially uncovered implant with respect to anatomical features of the urethra while using the imaging device; and
operating the actuator to further change the relative longitudinal position between the inner tube and the outer sleeve to deliver the implant in the urethra aligned with prostatic lobes of the urethra.

8. The method of claim 7, wherein the anatomical features comprise at least one of a prostatic lobe, a bladder neck, or a verumontanum.

9. The method of claim 7, wherein operating the actuator to change the relative longitudinal position between the inner tube and the outer sleeve comprises moving a safety catch.

10. The method of claim 7, wherein inserting the distal end of the outer sleeve of the implant delivery device through the urethra comprises steering the delivery device.

11. The method of claim 7, wherein after delivering the implant in the urethra the implant is between a bladder neck and an external sphincter.

12. The method of claim 7, wherein the inner tube comprises a proximal protrusion and a distal protrusion, and wherein the space comprises a gap between the proximal protrusion and the distal protrusion.

13. The method of claim 7, wherein the inner tube comprises a plurality of spaces each engaging one of the plurality of proximal apices of the implant.

14. The method of claim 7, wherein the anatomical features comprise at least one of a prostatic lobe, a bladder neck, or a verumontanum, wherein inserting the distal end of the outer sleeve of the implant delivery device through the urethra comprises steering the delivery device, and wherein after delivering the implant in the urethra the implant is between a bladder neck and an external sphincter.

15. A method of treating benign prostatic hyperplasia, the method comprising:
inserting a distal end of an outer sleeve of an implant delivery device through a urethra,
 the outer sleeve comprising a hollow distal segment holding an implant in a contracted state,
 the implant expandable from the contracted state to an expanded state,
 the delivery device comprising a handle comprising an actuator,
 the outer sleeve extending distally from the handle, and
 the delivery device comprising an imaging device;
operating the actuator to partially uncover the implant; and
rotationally orienting the partially uncovered implant with respect to anatomical features of the urethra while using the imaging device.

16. The method of claim 15, wherein the anatomical features comprise at least one of a prostatic lobe, a bladder neck, or a verumontanum.

17. The method of claim 15, wherein operating the actuator comprises moving a safety catch.

18. The method of claim 15, wherein inserting the distal end of the outer sleeve of the implant delivery device through the urethra comprises steering the delivery device.

19. The method of claim 15, further comprising operating the actuator to deliver the implant in the urethra.

20. The method of claim 19, wherein after delivering the implant in the urethra the implant is aligned with prostatic lobes of the urethra.

21. The method of claim 19, wherein after delivering the implant in the urethra the implant is between a bladder neck and an external sphincter.

22. The method of claim 15, wherein operating the actuator to partially uncover the implant comprises proximally retracting the imaging device.

23. The method of claim 22, wherein the proximally retracted imaging device provides a view of thea plurality of distal apices relative to the anatomical features of the urethra to aid orientation and placement of the implant.

24. The method of claim 22, wherein the proximally retracted imaging device provides a view from inside the a plurality of distal apices.

25. The method of claim 15, further comprising operating the actuator to deliver the implant in the urethra, wherein the anatomical features comprise at least one of a prostatic lobe, a bladder neck, or a verumontanum, and wherein inserting the distal end of the outer sleeve of the implant delivery device through the urethra comprises steering the delivery device.

26. The method of claim 7, wherein operating the actuator to change the relative longitudinal position between the inner tube and the outer sleeve comprises proximally retracting the imaging device.

27. The method of claim 26, wherein the proximally retracted imaging device provides a view from inside the plurality of distal apices.

* * * * *

UNITED STATES PATENT AND TRADEMARK OFFICE
CERTIFICATE OF CORRECTION

PATENT NO. : 11,484,398 B2
APPLICATION NO. : 17/654642
DATED : November 1, 2022
INVENTOR(S) : Riona Ni Ghriallais It is certified that error appears in the above-identified patent and that said Letters Patent is hereby corrected as shown below:

In the Claims

In Column 21, Claim 1, Line 67, delete "comprising;" and insert --comprising:--.

In Column 24, Claim 23, Line 38, delete "thea" and insert --a--.

In Column 24, Claim 24, Line 42, delete "the a" and insert --a--.

Signed and Sealed this
Twenty-first Day of February, 2023

Katherine Kelly Vidal
*Director of the United States Patent and Trademark Office*